United States Patent

Chakravarty et al.

Patent Number: 5,128,327
Date of Patent: Jul. 7, 1992

[54] ANGIOTENSIN II ANTAGONISTS INCORPORATING A NITROGEN CONTAINING SIX MEMBERED RING HETEROCYCLE

[75] Inventors: Prasun K. Chakravarty, Edison; Malcolm MacCross, Freehold; Nathan Mantlo; Thomas F. Walsh, both of Westfield, all of N.J.

[73] Assignee: Merck & Co., Inc., Rahway, N.J.

[21] Appl. No.: 674,836

[22] Filed: Mar. 25, 1991

[51] Int. Cl.$^5$ .................. A61K 31/435; C07D 471/04
[52] U.S. Cl. ..................................... 514/81; 514/234.5; 514/303; 544/127; 546/21; 546/23; 546/118
[58] Field of Search .......................... 546/118, 21, 23; 544/127; 514/303, 81, 234.5

[56] References Cited

FOREIGN PATENT DOCUMENTS

| | | |
|---|---|---|
| 58696/90 | 7/1989 | Australia . |
| 0253310 | 7/1987 | European Pat. Off. . |
| 0260613 | 9/1987 | European Pat. Off. . |
| 0323841 | 1/1989 | European Pat. Off. . |
| 0324377 | 1/1989 | European Pat. Off. . |
| 0392317 | 4/1990 | European Pat. Off. . |
| 0399731 | 5/1990 | European Pat. Off. . |
| 0399732 | 5/1990 | European Pat. Off. . |
| 400974 | 5/1990 | European Pat. Off. . |
| 0403158 | 6/1990 | European Pat. Off. . |
| 0403159 | 6/1990 | European Pat. Off. . |
| 0411766 | 6/1990 | European Pat. Off. . |
| 409332 | 7/1990 | European Pat. Off. . |
| 0412594 | 7/1990 | European Pat. Off. . |
| 0415886 | 8/1990 | European Pat. Off. . |
| 0419048 | 8/1990 | European Pat. Off. . |
| 0429257 | 11/1990 | European Pat. Off. . |
| 8911855 | 5/1989 | United Kingdom . |
| 9005843 | 3/1990 | United Kingdom . |

*Primary Examiner*—Bernard Dentz
*Attorney, Agent, or Firm*—Joseph F. DiPrima; William H. Nicholson; Valerie J. Camara

[57] ABSTRACT

There are disclosed compounds, containing a pyridine, pyrazine or pyrimidine functionality on the lower ring of Formula I, which are useful as angiotensin II antagonists.

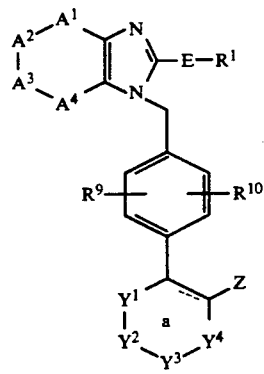

12 Claims, No Drawings

ANGIOTENSIN II ANTAGONISTS INCORPORATING A NITROGEN CONTAINING SIX MEMBERED RING HETEROCYCLE

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitivly blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, vol. 5, pp. 246-271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; and 4,582,847 in European Patent Applications 028,834; 245,637; 253,310; and 291,969; and in articles by A. T. Chiu, et al., [*Eur. J. Pharm. Exp. Therap.*, 157, 13–21 (1988)] and by P. C. Wong, et al., [*J. Pharm. Exp. Therap.*, 247, 1–7 (1988)]. All of the U.S. patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in this application have been identified in any U.S. patent, European Applications or articles. The substituted imidazoles, have been disclosed in European Patent Applications by DuPont (EPO 253,310 and EPO 324,377) focusing on the design of Angiotensin II Antagonists. Substituted benzimidazole containing compounds useful as angiotensin II antagonists have been disclosed in U.S. Pat. No. 4,880,804 and European Patent Application 392,317. Substituted imidazopyridine containing compounds useful as angiotensin II antagonists have also been disclosed in European Patent Applications 260,613, 399,731 and 421,848 and U.S. Ser. No. 516,286 (filed May 4, 1990).

BRIEF DESCRIPTION OF THE INVENTION

The compounds of formula (I) are angiotensin II antagonists and are useful in the treatment of hypertension and congestive heart failure. Additionally, pharmaceutically acceptable compositions of these novel compounds, as the sole therapeutically active ingredient and in combination with diuretics and other antihypertensive agents, including beta-blockers, angiotensin converting enzyme inhibitors, calcium channel blockers or a combination thereof are disclosed. Further, methods of treating hypertension, congestive heart failure and elevated intraocular pressure also are described.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

DETAILED DESCRIPTION OF THE INVENTION

This invention relates to compounds having the formula:

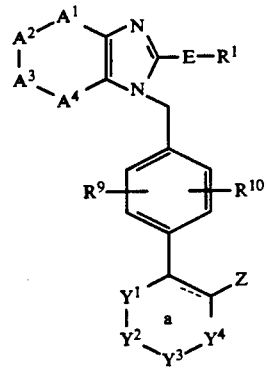

wherein:

$R^1$ is:
(a) $(C_1-C_6)$-alkyl, $(C_2-C_6)$-alkenyl or $(C_2-C_6)$-alkynyl each of which can be unsubstituted or substituted with a substituent selected from the group consisting of:
  i) aryl as defined below in $R^1(b)$,
  ii) $(C_3-C_7)$-cycloalkyl,
  iii) Cl, Br, I, F,
  iv) OH,
  v) $NH_2$,
  vi) $NH(C_1-C_4)$-alkyl,
  vii) $N[(C_1-C_4)$-alkyl$)]_2$,
  viii) $NHSO_2R^2$,
  ix) $CF_3$,
  x) $COOR^2$, or
  xi) $SO_2NHR^2$,
(b) aryl, wherein aryl is defined as phenyl or naphthyl, unsubstituted or substituted with 1 or 2 substitutents selected from the group consisting of:
  i) Cl, Br, I, F,
  ii) $(C_1-C_4)$-alkyl,
  iii) $(C_1-C_4)$-alkoxy,
  iv) $NO_2$
  v) $CF_3$ vi) SO$_2$NR$^2$R$^2$,
vii) (C$_1$-C$_4$)-alkylthio,
viii) hydroxy,
ix) amino,
x) (C$_3$-C$_7$)-cycloalkyl,
xi) (C$_3$-C$_{10}$)-alkenyl,
(c) heteroaryl, wherein heteroaryl is defined as a 5- or 6-membered heteroaromatic moiety, which can contain one or two members selected from the group consisting of N, O, S and wherein the heteroaryl is unsubstituted, monosubstituted or disubstituted with substituents selected from the group consisting of:
i) Cl, Br, I, F,
ii) OH,
iii) SH,
iv) NO$_2$,
v) (C$_1$-C$_4$)-alkyl,
vi) (C$_2$-C$_4$)-alkenyl,
vii) (C$_2$-C$_4$)-alkynyl,
viii) (C$_1$-C$_4$)-alkoxy, or
ix) CF$_3$,
(d) (C$_1$-C$_4$)-perfluoroalkyl, or
(e) (C$_3$-C$_7$)-cycloalkyl, which can be substituted or unsubstituted with a substitutent selected from the group consisting of: (C$_1$-C$_4$)-alkyl, (C$_1$-C$_4$)-perfluoroalkyl, Cl, Br, I or F;
—A$^1$—A$^2$—A$^3$—A$^4$— represents:

(a) 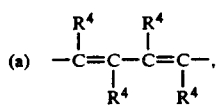

(b) 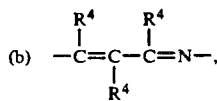

(c) 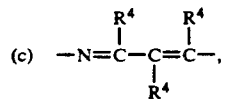

(d) 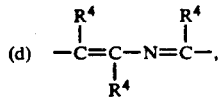

(e) 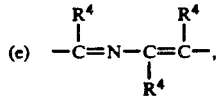

(f) 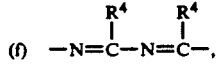

(g) 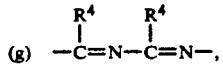

(h) 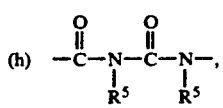

(i) 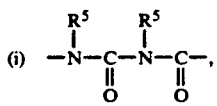

(j) 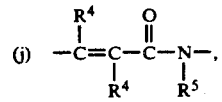

(k) 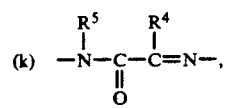

(l) 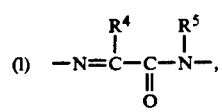

(m) 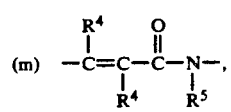

(n) 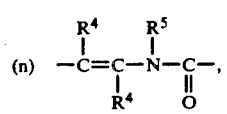

(o) 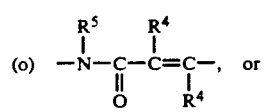, or (p) 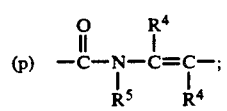;

E is:
(a) a single bond,
(b) —S(O)$_n$(CH$_2$)$_s$—, or
(c) —O—;
n is 0 to 2;
s is 0 to 5;
R$^2$ is:
(a) H,
(b) (C$_1$-C$_6$)-alkyl,
(c) —CH$_2$—O—C(O)CH$_3$,
(d) CH$_2$-aryl, or
(e) aryl;
R$^4$ groups are independently:
(a) H,
(b) (C$_1$-C$_6$)-alkyl, (C$_2$-C$_6$)-alkenyl, (C$_2$-C$_6$)-alkynyl or (C$_3$-C$_8$)-cycloalkyl, each of which is unsubstituted or substituted with:
i) OH,
ii) (C$_1$-C$_4$)-alkoxy,
iii) CO$_2$R$^2$,
iv) OCOR$^2$,
v) CONHR$^2$,
vi) CON(R$^2$)$_2$,
vii) N(R$^2$)C(O)R$^2$,
viii) NH$_2$,
ix) (C$_1$-C$_4$)-alkylamino,
x) di[(C$_1$-C$_4$)-alkyl]amino,
xi) aryl,
xii) heteroaryl,
(c) —C(O)-aryl,
(d) —NO$_2$,
(e) Cl, Br, I, F, (f) —OH,
(g) —OR$^{16}$,
(h) (C$_1$-C$_4$)-perfluoroalkyl,
(i) —SH,
(j) —S(O)$_n$—(C$_1$-C$_4$)-alkyl,
(k) —CO$_2$R$^2$,
(l) —SO$_3$H,
(m) —NR$^2$R$^{16}$,
(n) —NR$^2$C(O)R$^{16}$,
(o) —NR$^2$COOR$^{14}$,
(p) —SO$_2$NHR$^{14}$,
(q) —SO$_2$NR$^2$R$^2$,
(r) —NHSO$_2$R$^{14}$,
(s) —C(O)NHSO$_2$R$^{14}$,
(t) aryl,
(u) heteroaryl,
(v) morpholin-4-yl,
(w) CONH$_2$, or
(y) 1H-tetrazol-5-yl;

R$^5$ is:
(a) H,
(b) (C$_1$-C$_6$)-alkyl, (C$_2$-C$_6$)-alkenyl or (C$_2$-C$_6$)-alkynyl each of which can be unsubstituted or substituted with a substituent selected from the group consisting of: (C$_3$-C$_7$)-cycloalkyl, Cl, Br, I, F, —OH, —NH$_2$, —NH[(C$_1$-C$_4$)-alkyl], —N[(C$_1$-C$_4$)-alkyl]$_2$, —NHSO$_2$R$^{18}$, —CO$_2$R$^{18}$, (C$_1$-C$_4$)-alkoxy, (C$_1$-C$_4$)-alkylthio, (C$_1$-C$_4$)-acyl, or C(=O)NH$_2$,
(c) aryl, unsubstituted or substituted with V or W as defined below, or
(d) aryl-(C$_1$-C$_4$)-alkyl, unsubstituted or substituted with V or W as defined below;

—Y$^1$—Y$^2$—Y$^3$—Y$^4$— is:
(a) —N=CR$^{11}$—CR$^{11}$=CR$^{11}$—,
(b) —CR$^{11}$=N—CR$^{11}$=CR$^{11}$—,
(c) —CR$^{11}$=CR$^{11}$—N=CR$^{11}$—,
(d) —CR$^{11}$=CR$^{11}$—CR$^{11}$=N—,
(e) —N=CR$^{11}$—N=CR$^{11}$—,
(f) —CR$^{11}$=N—CR$^{11}$=N—,
(g) —N=N—CR$^{11}$=CR$^{11}$—,
(h) —CR$^{11}$=N—N=CR$^{11}$—,
(i) —CR$^{11}$—CR$^{11}$—N=N—,
(j) —N=CR$^{11}$—CR$^{11}$=N—,

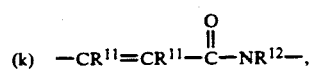

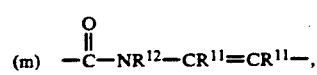

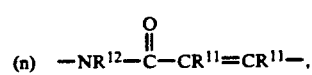

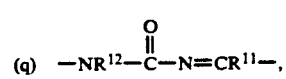

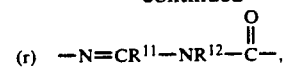

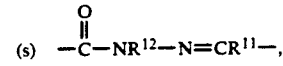

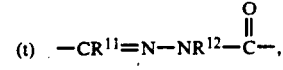

wherein a represents a double bond in each of the above definitions [(a) thru (t)]

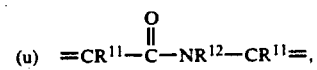

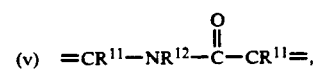

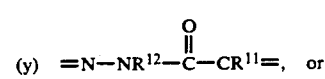

wherein a represents a single bond in each of the above definitions [(u) thru (z)];

R$^9$ and R$^{10}$ are each independently:
(a) h,
(b) Cl, Br, I, F,
(c) NO$_2$,
(d) (C$_1$-C$_6$)-alkyl,
(e) (C$_1$-C$_6$)-acyloxy,
(f) (C$_3$-C$_6$)-cycloalkyl,
(g) (C$_1$-C$_6$)-alkoxy,
(h) —NHSO$_2$R$^2$,
(i) hydroxy-(C$_1$-C$_4$)-alkyl,
(j) aryl-(C$_1$-C$_4$)-alkyl,
(k) (C$_1$-C$_4$)-alkylthio,
(l) (C$_1$-C$_4$)-alkylsulfinyl,
(m) (C$_1$-C$_4$)-alkylsulfonyl,
(n) NH$_2$,
(o) (C$_1$-C$_4$)-alkylamino,
(p) (C$_1$-C$_4$)-dialkylamino,
(q) CF$_3$,
(r) —SO$_2$NHR$^2$,
(s) furyl,
(t) aryl, wherein aryl is phenyl or naphthyl, unsubstituted or substituted with one or two substituents selected from the group consisting of: Cl, Br, I, F, (C$_1$-C$_4$)-alkyl, (C$_1$-C$_4$)-alkoxy, NO$_2$, CF$_3$, (C$_1$-C$_4$)-alkythio, OH, NH$_2$, —NH[(C$_1$-C$_4$)-alkyl], —N[(C$_1$-C$_4$)-alkyl]$_2$, —CO$_2$H, or —CO$_2$—(C$_1$-C$_4$)-alkyl, or
(u) when R$^9$ and R$^{10}$ are bonded to adjacent carbon atoms, they can be joined to form an aryl ring;

R$^{11}$ is:
(a) H,
(b) Cl, Br, I, F,
(c) NO$_2$, (d) $NH_2$,
(e) $(C_1-C_4)$-alkylamino,
(f) di-$(C_1-C_4$-alkyl)amino
(g) $SO_2NHR^2$,
(h) $CF_3$,
(i) $(C_1-C_4)$-alkyl,
(j) $(C_1-C_4)$-alkoxy, or
(k) when two $R^{11}$ substitutents are bonded to adjacent carbon atoms, they can be joined to form an aryl ring;

$R^{12}$ is:
(a) H,
(b) phenyl or —$CH_2$-phenyl, in which the phenyl is unsubstituted or substituted with one or two substituents selected from the group consisting of: Cl, Br, I, F, $(C_1-C_4)$-alkyl, or $(C_1-C_4)$-alkoxy, $CF_3$, $NH[(C_1-C_4)$-alkyl]$, $N[(C_1-C_4)$-alkyl]$_2$, $NH_2$ or $CO_2R^2$;

Z is:
(a) —$CO_2R^2$,
(b) —$SO_3R^{13}$,
(c) —$NHSO_2R^{14}$,
(d) —$PO(OR^{13})_2$,
(e) —$SO_2NHR^{14}$,
(f) —$CONHOR^{13}$, (g) 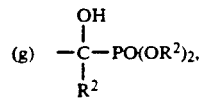

(h) —CN,
(i) —$SO_2NH$-heteroaryl, wherein heteroaryl is an unsubstituted, monosubstituted or disubstituted five or six membered aromatic ring which can contain from 1 to 3 heteroatoms selected from the group consisting of O, N or S and wherein the substituents are members selected from the group consisting of: —OH, —SH, —$(C_1-C_4)$-alkyl, —$(C_1-C_4)$-alkoxy, —$CF_3$, Cl, Br, F, I, —$NO_2$, —$CO_2H$, —$CO_2$—$(C_1-C_4)$-alkyl, —$NH_2$, $NH[(C_1-C_4)$-alkyl]$ or —$N[(C_1-C_4)$-alkyl]$_2$,
(j) —$CH_2SO_2NH$-heteroaryl,
(k) —$SO_2NHC(O)R^{14}$,
(l) —$CH_2SO_2NHC(O)R^{14}$,
(m) —$C(O)NHSO_2R^{14}$,
(n) —$CH_2C(O)NHSO_2R^{14}$,
(o) —$NHSO_2NHC(O)R^{14}$,
(p) —$NHC(O)NHSO_2R^{14}$, (q) 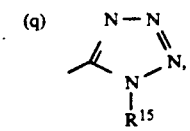

(r) 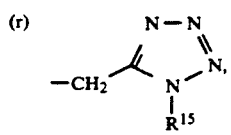

(s) 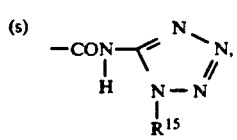

(t) —$CONHNHSO_2CF_3$, (u) 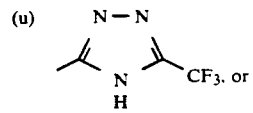

(v) 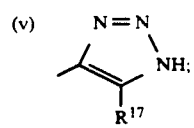

$R^{13}$ is H, —$CH_2$-phenyl or —$CH(R^4)$—O—$C(O)R^4$;
$R^{14}$ is
(a) aryl,
(b) heteroaryl,
(c) $(C_3-C_7)$-cycloalkyl,
(d) $(C_1-C_4)$-alkyl, unsubstituted or substituted with a substituent selected from the group consisting of: aryl, heteroaryl, —OH, —SH, $(C_1-C_4)$-alkyl, $(C_1-C_4)$-alkoxy, $(C_1-C_4)$-alkylthio, —$CF_3$, Cl, Br, F, I, —$NO_2$, —$CO_2H$, $CO_2$—$(C_1-C_4)$-alkyl, —$NH_2$, —$N[(C_1-C_4)$-alkyl]$_2$, —$NH[(C_1-C_4)$-alkyl]$, —$PO_3H$ or $PO(OH)(C_1-C_4)$-alkoxy, or
(e) $(C_1-C_4)$-perfluoroalkyl;
$R^{15}$ is
(a) H,
(b) $(C_1-C_6)$-alkyl,
(c) $(C_2-C_4)$-alkenyl,
(d) $(C_1-C_4)$-alkoxyalkyl,
(e) —$CH_2$—O—$C(O)CH_3$, or
(f) —$CH_2$-phenyl, wherein the phenyl is unsubstituted or substituted with a substituent selected from the group consisting of: —$NO_2$, —$NH_2$, —OH or —$OCH_3$;
$R^{16}$ is:
(a) H, or
(b) $(C_1-C_4)$-alkyl unsubstituted or substituted with:
i) $NH_2$,
ii) $NH[(C_1-C_4)$-alkyl]$,
iii) $N[(C_1-C_4)$-alkyl]$_2$,
iv) $CO_2H$,
v) $CO_2(C_1-C_4)$-alkyl,
vi) OH,
vii) $SO_3H$, or
viii) $SO_2NH_2$;
$R^{17}$ is —CN, —$NO_2$, —$CO_2R^2$, $(C_1-C_6)$-perfluoroalkyl or —$CF_3$;
$R^{18}$ is:
(a) H,
(b) $(C_1-C_6)$-alkyl,
(c) aryl, or
(d) $(C_1-C_5)$-alkyl-aryl; and
V and W are each independently selected from:
(a) H,
(b) $(C_1-C_5)$-alkoxy,
(c) $(C_1-C_5)$-alkyl,
(d) hydroxy,
(e) $(C_1-C_5)$-alkyl-$S(O)_n$,
(f) —CN,
(g) —$NO_2$,
(h) —$NR^2R^2$,
(i) $(C_1-C_5)$-acyl-$NR^2R^2$,
(j) —$CO_2R^2$,
(k) $(C_1-C_5)$-alkyl-carbonyl,
(l) $CF_3$, (m) I, Br, Cl, F,
(n) hydroxy-$(C_1-C_4)$-alkyl-,
(o) carboxy-$(C_1-C_4)$-alkyl-,
(p) —1H-tetrazol-5-yl,
(q) —NH—$SO_2CF_3$, or
(r) aryl; and the pharmaceutically acceptable salts thereof.

One embodiment of the compounds of Formula I are those wherein:

$R^1$ is:
(a) $(C_1-C_6)$-alkyl, $(C_2-C_6)$-alkenyl or $(C_2-C_6)$-alkynyl each of which can be unsubstituted or substituted with a substituent selected from the group consisting of:
  i) aryl, wherein aryl is defined as phenyl or naphthyl, unsubstituted or substituted with 1 or 2 substituents selected from the group consisting of: Cl, Br, I, F, $(C_1-C_4)$-alkyl, $(C_1-C_4)$-alkoxy, $NO_2$, $CF_3$, $SO_2NR^2R^2$, $(C_1-C_4)$-alkylthio, hydroxy, amino, $(C_3-C_7)$-cycloalkyl, or $(C_3-C_{10})$-alkenyl,
  ii) $(C_3-C_7)$-cycloalkyl,
  iii) Cl, Br, I, F,
  iv) OH,
  v) $NH_2$,
  vi) $NH(C_1-C_4)$-alkyl,
  vii) $N[(C_1-C_4)$-alkyl$)]_2$,
  viii) $NHSO_2R^2$,
  ix) $CF_3$,
  x) $COOR^2$, or
  xi) $SO_2NHR^2$;
(b) $(C_1-C_4)$-perfluoroalkyl, or
(c) $(C_3-C_7)$-cycloalkyl, which can be substituted or unsubstituted with a substituent selected from the group consisting of: $(C_1-C_4)$-alkyl, $(C_1-C_4)$-perfluoroalkyl, Cl, Br, I or F;

—$A^1$—$A^2$—$A^3$—$A^4$— represent:

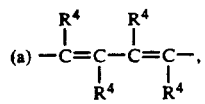

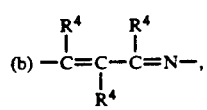

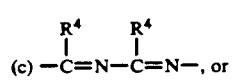

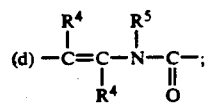

E is: a single bond;

$R^2$ is:
(a) H,
(b) $(C_1-C_6)$-alkyl,
(c) —$CH_2$—O—$C(O)CH_3$,
(d) $CH_2$-aryl, or
(e) aryl;

$R^4$ groups are independently:
(a) H,
(b) $(C_1-C_6)$-alkyl, $(C_2-C_6)$-alkenyl, $(C_2-C_6)$-alkynyl or $(C_3-C_8)$-cycloalkyl, each of which is unsubstituted or substituted with:
  i) OH,
  ii) $(C_1-C_4)$-alkoxy,
  iii) $CO_2R^2$,
  iv) $OCOR^2$,
  v) $CONHR^2$,
  vi) $CON(R^2)_2$,
  vii) $N(R^2)C(O)R^2$,
  viii) $NH_2$,
  ix) $(C_1-C_4)$-alkylamino,
  x) di$[(C_1-C_4)$-alkyl]amino,
  xi) aryl,
  xii) heteroaryl,
(c) —C(O)-aryl,
(d) —$NO_2$,
(e) Cl, Br, I, F,
(f) —OH,
(g) —$OR^{16}$,
(h) —$CF_3$,
(i) —SH,
(j) —$S(O)_n$—$(C_1-C_4)$-alkyl,
(k) —$CO_2R^2$,
(l) —$SO_3H$,
(m) —$NR^2R^{16}$,
(n) —$NR^2C(O)R^{16}$,
(o) —$NR^2COOR^{14}$,
(p) —$SO_2NHR^{14}$,
(q) —$SO_2NR^2R^2$,
(r) —$NHSO_2R^{14}$,
(s) —$C(O)NHSO_2R^{14}$,
(t) aryl,
(u) heteroaryl, or
(v) morpholin-4-yl; and $R^5$ is:
(a) H,
(b) $(C_1-C_6)$-alkyl, $(C_2-C_6)$-alkenyl or $(C_2-C_6)$-alkynyl each of which can be unsubstituted or substituted with a substituent selected from the group consisting of: $(C_3-C_7)$-cycloalkyl, Cl, Br, I, F, —OH, —$NH_2$, —$NH[(C_1-C_4)$-alkyl], —$N[(C_1-C_4)$-alkyl]$_2$, —$NHSO_2R^{18}$, —$CO_2R^{18}$, $(C_1-C_4)$-alkoxy, $(C_1-C_4)$-alkylthio, $(C_1-C_4)$-acyl, or $C(=O)NH_2$,
(c) aryl, unsubstituted or substituted with V or W as defined below, or
(d) aryl-$(C_1-C_4)$-alkyl, unsubstituted or substituted with V or W as defined below;

—$Y^1$—$Y^2$—$Y^3$—$Y^4$— is:
(a) —N=$CR^{11}$—$CR^{11}$=$CR^{11}$—,
(b) —$CR^{11}$=N—$CR^{11}$=$CR^{11}$—,
(c) —$CR^{11}$=$CR^{11}$—N=$CR^{11}$—, or
(d) —$CR^{11}$=$CR^{11}$—$CR^{11}$=N—, wherein a represents a double bond in each of the above definitions [(a) thru (d)];

$R^9$ and $R^{10}$ are each independently:
(a) H,
(b) Cl, Br, I, F,
(c) $CF_3$,
(d) $(C_1-C_6)$-alkyl,
(e) $(C_1-C_6)$-acyloxy,
(f) $(C_3-C_6)$-cycloalkyl,
(g) $(C_1-C_6)$-alkoxy,
(h) hydroxy-$(C_1-C_4)$-alkyl,
(i) aryl-$(C_1-C_4)$-alkyl,
(j) $(C_1-C_4)$-alkylthio,
(k) $(C_1-C_4)$-alkylsulfinyl,
(l) $(C_1-C_4)$-alkylsulfonyl, or
(m) when $R^9$ and $R^{10}$ are bonded to adjacent carbon atoms, they can be joined to form an aryl ring;

$R^{11}$ is:
(a) H,
(b) Cl, Br, I, F,
(c) $NO_2$,
(d) $NH_2$,
(e) $(C_1-C_4)$-alkylamino,
(f) di-$(C_1-C_4$-alkyl)amino
(g) $SO_2NHR^2$,
(h) $CF_3$,
(i) $(C_1-C_4)$-alkyl,
(j) $(C_1-C_4)$-alkoxy, or
(k) when two $R^{11}$ substituents are bonded to adjacent carbon atoms, they can be joined to form an aryl ring;

$R^{12}$ is:
(a) H,
(b) $(C_1-C_4)$-alkyl, or
(c) phenyl or —$CH_2$-phenyl, in which the phenyl is unsubstituted or substituted with one or two substituents selected from the group consisting of: Cl, Br, I, F, $(C_1-C_4)$-alkyl, or $(C_1-C_4)$-alkoxy, $CF_3$, $NH[(C_1-C_4)$-alkyl], $N[(C_1-C_4)$-alkyl]$_2$, $NH_2$ or $CO_2R^2$;

Z is:
(a) —$CO_2R^2$,
(b) —CN,
(c) —$SO_2NH$-heteroaryl, wherein heteroaryl is an unsubstituted, monosubstituted or disubstituted five or six membered aromatic ring which can contain from 1 to 3 heteroatoms selected from the group consisting of O, N or S and wherein the substituents are members selected from the group consisting of: —OH, —SH, —$(C_1-C_4)$-alkyl, —$(C_1-C_4)$-alkoxy, —$CF_3$, Cl, Br, F, I, —$NO_2$, —$CO_2H$, —$CO_2$—$(C_1-C_4)$-alkyl, —$NH_2$, $NH[(C_1-C_4)$-alkyl] or —$N[(C_1-C_4)$-alkyl]$_2$,
(d) —$CH_2SO_2NH$-heteroaryl,
(e) —$SO_2NHC(O)R^{14}$,
(f) —$C(O)NHSO_2R^{14}$,
(g) —$NHSO_2R^{14}$, or
(h) —1H-tetrazol-5-yl;

$R^{14}$ is
(a) aryl,
(b) heteroaryl,
(c) $(C_3-C_7)$-cycloalkyl,
(d) $(C_1-C_4)$-alkyl, unsubstituted or substituted with a substituent selected from the group consisting of: aryl, heteroaryl, —OH, —SH, $(C_1-C_4)$-alkyl, $(C_1-C_4)$-alkoxy, $(C_1-C_4)$-alkylthio, —$CF_3$, Cl, Br, F, I, —$NO_2$, —$CO_2H$, $CO_2$-$(C_1-C_4)$-alkyl, —$NH_2$, —$N[(C_1-C_4)$-alkyl]$_2$, —$NH[(C_1-C_4)$-alkyl], —$PO_3H$, PO(OH)$(C_1-C_4)$-alkyoxy, or
(e) $(C_1-C_4)$-perfluoroalkyl;

$R^{16}$ is:
(a) H, or
(b) $(C_1-C_4)$-alkyl unsubstituted or substituted with:
i) $NH_2$,
ii) $NH[(C_1-C_4)$-alkyl],
iii) $N[(C_1-C_4)$-alkyl]$_2$,
iv) $CO_2H$,
v) $CO_2(C_1-C_4)$-alkyl,
vi) OH,
vii) $SO_3H$, or
viii) $SO_2NH_2$;

$R^{18}$ is:
(a) H,
(b) $(C_1-C_6)$-alkyl,
(c) aryl, or
(d) aryl-$(C_1-C_5)$-alkyl;

V and W are each independently selected from:
(a) H,
(b) $(C_1-C_5)$-alkoxy,
(c) $(C_1-C_5)$-alkyl,
(d) hydroxy,
(e) $(C_1-C_5)$-alkyl-$S(O)_n$,
(f) —CN,
(g) —$NO_2$,
(h) —$NR^2R^2$,
(i) $(C_1-C_5)$-acyl-$NR^2R^2$,
(j) —$CO_2R^2$,
(k) $(C_1-C_5)$-alkyl-carbonyl,
(l) $CF_3$,
(m) I, Br, Cl, F,
(n) hydroxy-$(C_1-C_4)$-alkyl-,
(o) carboxy-$(C_1-C_4)$-alkyl-,
(p) —tetrazol-5-yl,
(q) —$NHSO_2CF_3$, or
(r) aryl; and
the pharmaceutically acceptable salts thereof.

The alkyl substituents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The aryl substituent recited above represents phenyl or naphthyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

Exemplifying this class are the following compounds:
7-methyl-2-propyl-3-[[4-[2-(1H-tetrazol[e]-5-yl)-3-pyridinyl]phenyl]methyl]imidazo[4,5-b]pyridine.
5,7-dimethyl-2-propyl-3-[[4-[2-(1H-tetrazol[e]-5-yl)-3-pyridinyl]phenyl]methyl]imidazo[4,5-b]pyridine.
5,7-dimethyl-2-ethyl-3-[[4-3-(1H-tetrazol[e]-5-yl)-2-pyridinyl]phenyl]methyl]imidazo[4,5-b]pyridine.
7-methyl-2-propyl-3-[[4-[2-(N-benzoylsulfonamido)-3-pyridinyl]phenyl]methyl]imidazo[4,5-b]pyridine.
5,7-dimethyl-2-propyl-3-[[4-[2-(N-cyclopropanecarbonylsulfonamido)-3-pyridinyl]phenyl]methyl]imidazo[4,5-b]pyridine.
7-methyl-2-propyl-3-[[4-[3-(1H-tetrazol[e]-5-yl)-2-pyridinyl]phenyl]methyl]imidazo[4,5-b]pyridine-5-carboxylic acid.
2-ethyl-7-methyl-3-[[4-[3-(1H-tetrazol[e]-5-yl)-2-pyridinyl]phenyl]methyl]imidazo[4,5-b]pyridine-5-carboxylic acid.
7-methyl-2-propyl-3-[[4-[3-(1H-tetrazol[e]-5-yl)-2-pyridinyl]phenyl]methyl]imidazo[4,5-b]pyridine.
7-methyl-2-propyl-3-[[4-[3-(N-benzoylsulfonamido)-2-pyridinyl]phenyl]methyl]imidazo[4,5-b]pyridine.
7-methyl-2-ethyl-3-[[4-[3-(N-benzoylsulfonamido)-2-pyridinyl]phenyl]methyl]imidazo[4,5-b]pyridine.

7-methyl-2-propyl-3-[[4-[3-(N-benzoylsulfonamido)-2-pyridinyl]phenyl]methyl]imidazo[4,5-b]pyridine.

5,7-dimethyl-2-ethyl-3-[[4-[3-(N-cyclopropanecarbonylsulfonamido)-2-pyridinyl]phenyl]methyl]imidazo[4,5-b]pyridine.

7-methyl-2-propyl-3-[[4-[3-(1H-tetrazol[e]-5-yl)-4-pyridinyl]phenyl]methyl]imidazo[4,5-b]pyridine.

7-methyl-2-ethyl-3-[[4-[3-(1H-tetrazol[e]-5-yl)-4-pyridinyl]phenyl]methyl]imidazo[4,5-b]pyridine.

5,7-dimethyl-2-ethyl-3-[[4-[3-(1H-tetrazol[e]-5-yl)-4-pyridinyl]phenyl]methyl]imidazo[4,5-b]pyridine.

2-ethyl-7-methyl-3-[[4-[3-(1H-tetrazol[e]-5-yl)-4-pyridinyl]phenyl]methyl]imidazo[4,5-b]pyridine-5-carboxylic acid.

ethyl 2-ethyl-7-methyl-3-[[4-[3-(1H-tetrazol[e]-5-yl)-4-pyridinyl]phenyl]methyl]imidazo[4,5-b]pyridine-5-carboxylate.

5,7-dimethyl-2-ethyl-3-[[4-[3-(N-benzosulfonamido)-4-pyridinyl]phenyl]methyl]imidazo[4,5-b]pyridine.

5,7-dimethyl-2-ethyl-3-[[4-[3-(N-cyclopropanecarbonylsulfonamido)-4-pyridinyl]phenyl]methyl]imidazo[4,5-b]pyridine.

2-ethyl-7-methyl-3-[[4-[3-(N-benzoylsulfonamido)-4-pyridinyl]phenyl]methyl]imidazo[4,5-b]pyridine-5-carboxylic acid.

ethyl 2-ethyl-7-methyl-3-[[4-[3-(N-benzoylsulfonamido)-4-pyridinyl]phenyl]methyl]imidazo[4,5-b]pyridine-5-carboxylic acid.

2-ethyl-7-methyl-3-[[4-[3-(N-cyclopropanecarbonylsulfonamido)-4-pyridinyl]phenyl]methyl]imidazo[4,5-b]pyridine-5-carboxylic acid.

ethyl 2-ethyl-7-methyl-3-[[4-[3-(N-cyclopropanecarbonylsulfonamido)-4-pyridinyl]phenyl]methyl]imidazo[4,5-b]pyridine-5-carboxylate.

5,7-dimethyl-2-ethyl-3-[[4-[3-(trifluoromethanesulphonamido)-4-pyridinyl]phenyl]methyl]imidazo[4,5-b]pyridine.

5,7-dimethyl-2-ethyl-3-[[4-[3-[(2,6-difluorobenzene)-sulphonamido)-4-pyridinyl]phenyl]methyl]imidazo[4,5-b]pyridine.

5,7-dimethyl-2-ethyl-3-[[4-[3-(N-phenylsulfonylcarboxamido)-4-pyridinyl]phenyl]methyl]imidazo[4,5-b]pyridine.

5,7-dimethyl-2-ethyl-3-[[4-[4-(1H-tetrazol[e]-5-yl)-3-pyridinyl]phenyl]methyl]imidazo[4,5-b]pyridine.

5,7-dimethyl-2-ethyl-3-[[4-[4-(trifluoromethanesulphonamido)-3-pyridinyl]phenyl]methyl]imidazo[4,5-b]pyridine.

5,7-dimethyl-2-ethyl-3-[[4-[4-(N-phenylsulfonylcarboxamido)-3pyridinyl]phenyl]methyl]imidazo[4,5-b]pyridine.

5,7-dimethyl-2-ethyl-3-[[4-[5-(1H-tetrazol[e]-5-yl)-4-pyrimidinyl]phenyl]methyl]imidazo[4,5-b]pyridine.

5,7-dimethyl-2-ethyl-3-[[4-[5-(N-phenylsulfonyl-carboxamido)-4-pyrimidinyl]phenyl]methyl]imidazo[4,5-b]pyridine.

5,7-dimethyl-2-ethyl-3-[[4-[5-(N-benzoylsulfonamido)-4-pyrimidinyl]phenyl]methyl]imidazo[4,5-b]pyridine.

5,7-dimethyl-2-ethyl-3-[[4-[4-(1H-tetrazol[e]-5-yl)-5-pyrimidinyl]phenyl]methyl]imidazo[4,5-b]pyridine.

5,7-dimethyl-2-ethyl-3-[[4-[4-(N-phenylsulfonylcarboxamido)-5-pyrimidinyl]phenyl]methyl]imidazo[4,5-b]pyridine.

5,7-dimethyl-2-ethyl-3-[[4-[4-(N-benzoylsulfonamido)-5-pyridinyl]phenyl]methyl]imidazo[4,5-b]pyridine.

2-propyl-4-methyl-1-[[4-[3-(1H-tetrazol[e]-5-yl)-4-pyridinyl]phenyl]methyl]benzimidazole.

2-propyl-4,6-dimethyl-1-[[4-[3-(1H-tetrazol[e]-5-yl)-4-pyridinyl]phenyl]methyl]benzimidazole.

2-ethyl-4,6-dimethyl-1-[[4-[3-(1H-tetrazol[e]-5-yl)-4-pyridinyl]phenyl]methyl]benzimidazole.

2-propyl-4,7-dimethyl-1-[[4-[3-(1H-tetrazol[e]-5-yl)-4-pyridinyl]phenyl]methyl]benzimidazole.

2-propyl-5,6-dimethyl-1-[[4-[3-(1H-tetrazol[e]-5-yl)-4-pyridinyl]phenyl]methyl]benzimidazole.

2-propyl-4-methyl-1-[[4-[3-(1H-tetrazol[e]-5-yl)-4-pyridinyl]phenyl]methyl]benzimidazole-6-carboxylic acid.

2-propyl-4-methyl-1-[[4-[4-(1H-tetrazol[e]-5-yl)-3-pyridinyl]phenyl]methyl]benzimidazole-6-carboxylic acid.

2-propyl-4,6-dimethyl-1-[[4-[3-(N-phenylsulfonylcarboxamido)-4pyridinyl]phenyl]methyl]benzimidazole.

2-propyl-4,6-dimethyl-1-[[4-[3-(trifluoromethanesulphonamido)-4-pyridinyl]phenyl]methyl]benzimidazole.

2-propyl-4,6-dimethyl-1-[[4-[3-(2,6-difluorbenze)sulphonamido)-4-pyridinyl]phenyl]methyl]benzimidazole.

2-propyl-4,6-dimethyl-1-[[4-[3-(N-cyclopropanecarbonylsulphonamido)-4-pyridinyl]phenyl]methyl]benzimidazole.

6-methyl-2-(morpholin[e]-4-yl)-8-propyl-9-[[4-[3-(1H-tetrazol[e]-5-yl)-4-pyridinyl]phenyl]methyl]purine.

6-methyl-2-methylamino-8-propyl-9-[[4-[3-(1H-tetrazol[e]-5-yl)-4-pyridinyl[phenyl]methyl]purine.

2,6-dimethyl-8-propyl-9-[[4-[3-(1H-tetrazol[e]-5-yl)-4-pyridinyl]phenyl]methyl]purine.

2,6-dimethyl-8-ethyl-9-[[4-[3-(1H-tetrazol[e]-5-yl)-4-pyridinyl]phenyl]methyl]purine.

6-trifluoromethyl-2-methylamino-8-propyl-9[[4-[3-(1H-tetrazol[e]-5-yl)-4-pyridinyl]phenyl]methyl]purine.

6-methyl-2-(morpholin[e]-4-yl)-8-propyl-9-[[4-[3-(N-benzoylsulfonamido)-4-pyridinyl]phenyl]methyl]purine.

6-methyl-2-methylamino-8-propyl-9-[[4-[3-(N-benzoylsulfonamido)-4-pyridinyl]phenyl]methyl]purine.

2,6-dimethyl-8-propyl-9-[[4-[3-(N-benzoylsulfonamido)-4-pyridinyl]phenyl]methyl]purine.

GENERAL METHODS FOR PREPARING OF COMPOUNDS OF FORMULA I

The methods described in PART I AND PART II below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

It should be recognized that antagonists of Formula I consist of a heterocyclic component designated above by formula I and a substituted benzyl substitutent which is attached to the heterocyclic component at a nitrogen atom. Thus, two generally applicable approaches to antagonists of formula I are these:

1. A heterocycle, designated above in Formula I is prepared as described in PART I below. Then the heterocycle is alkylated at a nitrogen atom with a substituted benzyl halide or pseudohalide giving an alkylated heterocycle in the Schemes below, this alkylating agent is often designated as "Ar—CH$_2$Q" where Q is a halide (—Cl, Br, I) or pseudohalide (—OMs, OTs, OTf). In some cases, alkylation may take place at more than one nitrogen atom of the heterocycle, and in these cases, separation by fractional crystallization or by chromotographic methods may be necessary for isolation of the desired product. In some cases, the alkylation step produces a fully-assembled antagonist of Formula I, except that functional groups in the alkylating agent or in the heterocycle may be present in protected form and require deprotection steps to be carried out to complete the synthesis. In other cases, the alkylation is carried out with a substituted benzylic halide or pseudohalide ("Ar—CH$_2$Q"), but here the alkylation step is followed by subsequent steps which are required to assemble the substituted benzyl element of the antagonist of Formula I. The alkylation steps and subsequent steps used to prepare antagonists of Formula I, are described in PART II below.

The compounds of this invention maybe resolved using techniques known in the art. The diastereomeric salts or esters of the enantiomers are separated and the desired compound is the more active stereoisomer. The compounds of this invention, their pharmaceutically acceptable salts and their prodrug forms are included within the scope of this invention. Abbreviations used in the schemes and examples are listed in Table 1.

TABLE 1

| Reagents | |
|---|---|
| NBS | N-bromosuccinimide |
| AIBN | Azo(bis) isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluoroacetic acid |
| TMS-Cl | trimethylsilyl chloride |
| Im | imidazole |
| AcSK | potassium thioacetate |
| p-TsOH | p-toluenesulfonic acid |
| FMOC-Cl | 9-Fluorenylmethyloxycarbonyl chloride |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | OSO$_2$CF$_3$ |
| Ph | phenyl |
| FAB-MS (FSBMS) | Fast atom bombardment mass spectroscopy |
| NOE | Nuclear Overhauser Effect |
| SiO$_2$ | silica gel |
| trityl | triphenylmethyl |

PART I: PREPARATION OF THE HETEROCYCLES SHOWN IN FORMULA I

A. Preparation of the Benzimidazoles

Benzimidazoles

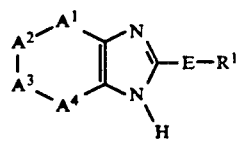

Compounds of Formula I which incorporate a benzimidazole heterocycle can be synthesized using the reactions and techniques described herein below. The reactions are performed in a solvent appropriate to the reagents and materials employed and suitable for the transformation being effected. It is understood by those skilled in the art of organic synthesis that the functionality present on the benzimidazole and other parts of the structure should be consistent with the chemical transformations proposed. Depending upon the reactions and techniques employed, this may involve changing the order of synthetic steps, use of required protecting groups followed by deprotection, and activation of the benzylic position of the alkylating agents used to enable alkylation at the nitrogen on the imidazole part of benzimidazoles.

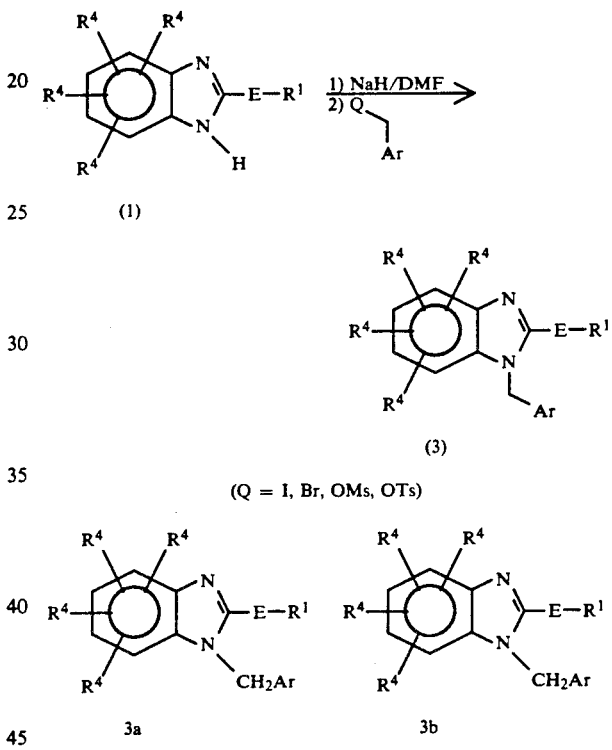

As shown in Scheme I-1, compounds of Formula (3) can be prepared by carrying out direct alkylation of alkali-metal salt of benzimidazole (1) (preparation of benzimidazoles are described in Schemes I-2 to I-5) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with metal alkoxide such as sodium or potassium methoxide, ethoxide or t-butoxide in an appropriate alcohol such as methanol, ethanol or t-butanol as the solvent. The alkylation is generally carried-out by dissolving the metal salt of benzimidazole in a dipolar aprotic solvent such as DMF or dimethylsulfoxide (DMSO) and reacting it with the alkylating agent at 20° C. to reflux temperature of the solvent for 1-24 hours.

If substituents on the benzene ring result in an unsymmetrical benzimidazole, the alkylation may produce a mixture of two regioisomers as products, which may be represented by formulas 3a and 3b, wherein the R$^4$ substituents of 3a are in reverse order to the R$^4$ substituents of 3b. These regioisomers possess distinct physicochemical and biological properties and in most cases can be separated and purified by using conventional separation techniques such as chromatography (flash column chromatograph, medium-pressure liquid chromatography, high pressure liquid chromatography (HPLC) and/or crystallization. In those cases where separation of regioisomers is difficult by conventional techniques, the mixture can be transformed into suitable derivatives that can be separated by usual separation methods. The structural assignments of the isomers can be made using proton NMR, Nuclear Overhauser Effect (NOE) experiments or X-ray crystallography.

SCHEME I-2

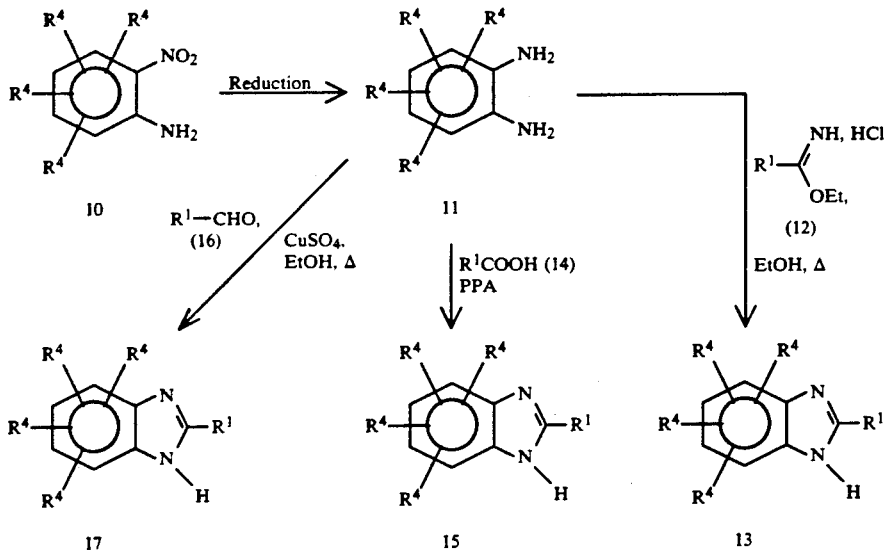

The starting benzimidazoles can be readily prepared by any of the standard procedures described in the literature [P. N. Preston, *Chemistry of Heterocyclic Compounds*, Vol. 40, part I, pp. 1-286 (1981) and references cited therein]. Several alternative routes to obtain benzimidazoles are outlined in Scheme I-2. The most widely used starting material, o-phenylenediamines (11), can be readily prepared from the corresponding o-nitroaniline (10) using standard reductive procedures such as metal-acid reduction or catalytic reduction. The substituted or unsubstituted (11) can then be treated with an appropriate imidate hydrochloride (12) to form corresponding benzimidazoles (13). Alternatively, the reaction of carboxylic acids (14) with o-phenylenediamines in the presence of polyphosphoric acid (PPA) is also effective in producing benzimidazoles (15). Benzimidazoles (17) can also be prepared from o-phenylenediamines and aldehyde (16) using cupric salt as an oxidant [R. Weidenhagen, *Chem. Ber.*, 69, 2263 (1936)].

SCHEME I-3

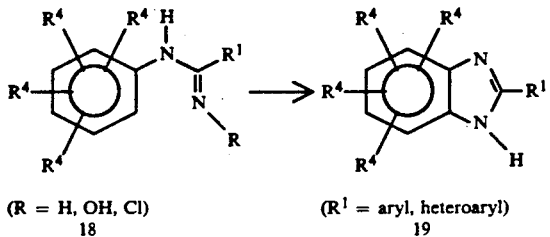

-continued
SCHEME I-3

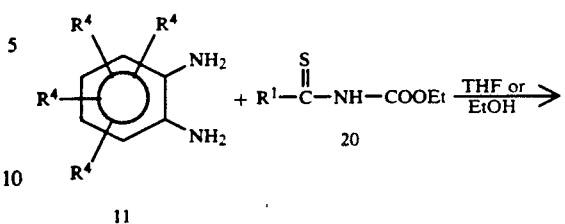

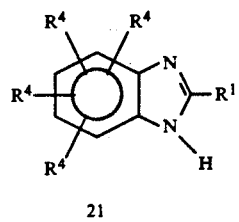

Although some benzimidazoles having aryl and heteroaryl groups at the 2 position can be prepared using the methods described in Scheme I-2, Scheme I-3 outlines methods which are more suitable for the synthesis of this class of compounds. N'-aryl-N-hydroxyamidines (18; R=OH) are cyclized under mild conditions using benzenesulfonyl chloride in pyridine or triethylamine to give 19 in a good yield [M. W. Partridge and H. A. Turner, *J. Chem. Soc.*, 2086 (1958)]. Parent amidines (18; R=H) can also be oxidized with sodium hypochlorite under basic conditions to form 19 [V. J. Grenda, R. E. Jones, G. Gal and M. Sletzinger, *J. Org. Chem.*, 30, 259, (1965)].

Alternatively, as shown in Scheme I-3, o-phenylenediamines (11) can be reacted with N-ethoxycarbonylthioamides (20) to give 2-substituted benzimidazoles (21) in excellent yields. This method avoids the use of acidic catalysts. The reagents (20) are easily obtained in one step from ethoxycarbonyl isothiocyanate and simple aromatic or heterocyclic compounds or alkylmagnesium halides [B. George and E. P.

Papadopoulos., *J. Org. Chem.*, 41, 3233 (1976); E. P. Papadopoulos., *J. Org. Chem.*, 41, 962 (1976)].

Derivatives, Part 1, " Wiley-Interscience, New York, 1953, pp. 285-291]. Carbonate esters, diethylpyrocar-

SCHEME I-4

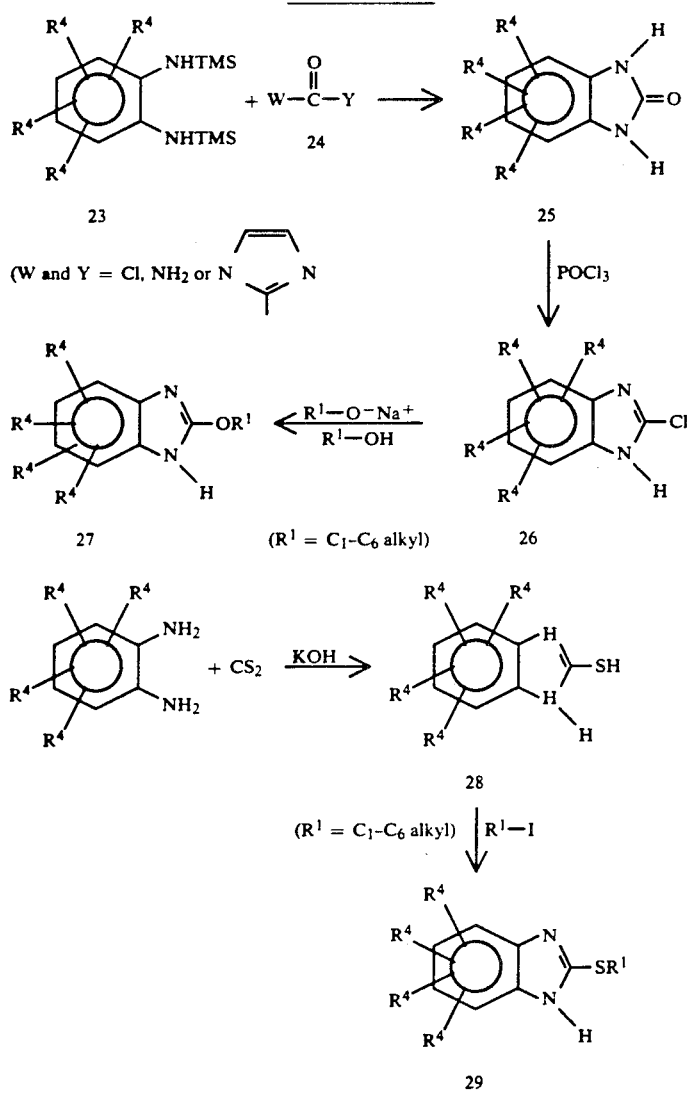

As outlined in Scheme I-4, benzimidazoles containing 2-alkoxy and thioalkyl substituents (27 and 29) can be prepared from the corresponding benzimidazolones (25) or benzimidazolethiones (28). Benzimidazolones are conveniently prepared from o-phenylenediamines and phosgene or urea [K. Hofmann, "Imidazole and its bonate, N,N-carbonyldiimidazole and N,N-diethylcarbamyl chloride may also be used in this reaction. The reaction of phosgene is apparently facilitated by the use of N,N'-bis-trimethylsilyl (TMS) derivative (23) instead of the parent diamine [L. Birkhofer, H. P. Kuhlthau, and A. Ritter, *Chem. Ber.*, 93, 2810 (1960)].

SCHEME I-5

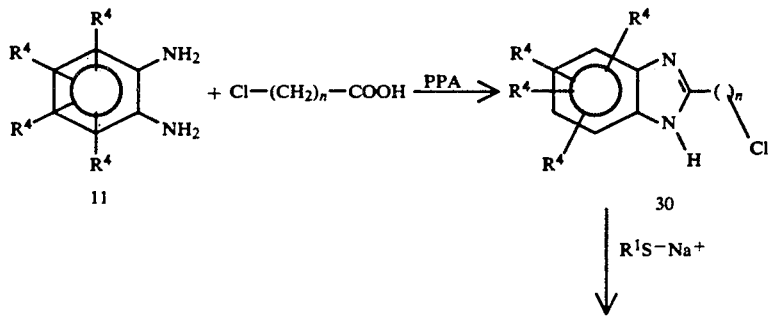

SCHEME I-5

(n = 1-3
R¹ = alkyl, alkyl-
aryl and alkyl-
heteroaryl)

(Q = I, Br, OMs, OTs)

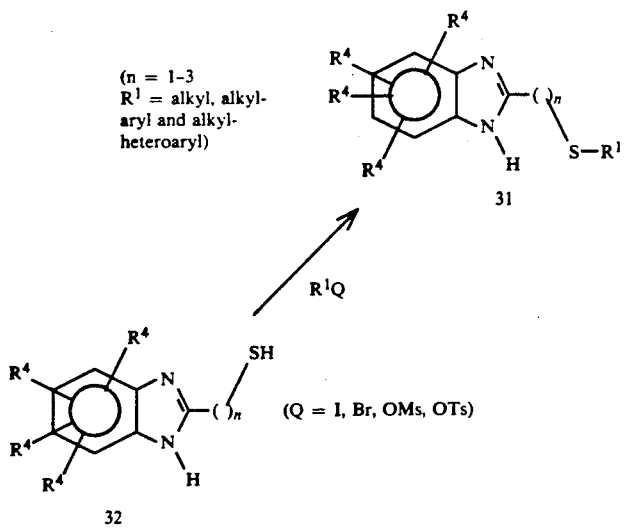

As described in Scheme I-5, 2-alkylthioalkyl substituted benzimidazoles (31) can be prepared from the reaction of RS-M (where M is sodium, potassium or lithium) with 2-chloroalkyl benzimidazoles (30). 2-Chloroalkyl benzimidazoles (30) can be conveniently prepared from the diamines and the chloroalkyl carboxylic acids using PPA [W. Knobloch, Chem. Ber., 91, 2557 (1958)]. Alternatively, compound 31 can also be prepared from the readily available 2-thioalkyl derivative (32) [E. S. Milner, S. Snyder, and M. M. Joulllie, J. Chem. Soc., 4151 (1964)].

Imidazo-6-Fused Heterocycles

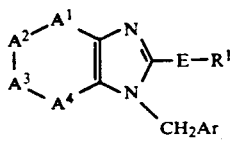

The compounds of Formula I can be synthesized using the reactions and techniques described herein below. The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

As shown in Reaction Scheme 1, compounds of Formula I can be prepared by carrying-out direct alkylation of alkali-metal salts of heterocycles (1) (preparation of heterocycles are described in Reaction Scheme 3-6) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with a metal alkoxide such as sodium or potassium methoxide, ethoxide or t-butoxide in an appropriate alcohol such as methanol, ethanol or t-butanol as the solvent. The alkylation is generally carried-out by dissolving the metal salt of the heterocycle in a dipolar aprotic solvent such as DMF or dimethylsulfoxide (DMSO) and reacting it with the alkylating agent at 20° C. to reflux temperature of the solvent for 1-24 hours.

If substituents and/or the hetero atom positions in the six membered ring are not symmetrically disposed, the alkylation on the imidazole nitrogen(s) can produce a mixture of two regioisomers as products arising from $N^1$ and $N^3$ alkylation. These regioisomers I and Ia possess distinct physico-chemical and biological properties and in most cases can be separated and purified by using conventional separation techniques such as chromatography (flash column chromatography, medium-pressure liquid chromatography, high performance liquid chromatography) and/or crystallization. In those cases where separation of regioisomers is difficult by conventional techniques, the mixture can be transformed into suitable derivatives that can be separated by the above separation methods. The structural assignments of the isomers can be made using Nuclear Overhauser Effect (NOE), $^1H$-$^{13}C$ coupled NMR experiments or X-ray crystallography.

When there is potential for alkylation of the 6-membered heterocyclic ring, this can be avoided by the use of suitable protecting groups.

The heterocycles of type (1) can be prepared by any of the standard procedures described in the literature [J. A. Montgomery and J. A. Secrist III in "Comprehensive Heterocyclic Chemistry," Vol. 5, A. R. Katritsky and C. W. Rees Eds., Pergamon Press 1984; pp 567-597 and 631-656 and references cited therein]. As shown in Scheme I-6, the most widely used starting materials are six member heterocyclic vicinal diamines (9). Fused imidazoles (10) can be prepared by condensation of (9) with an appropriate carboxylic acid, nitrile, imidate ester, or orthoester, either neat, or in a solvent appropriate and compatible with the starting materials and reagents, such as polyphosphoric acid, ethanol, methanol, hydrocarbon solvents, and with a catalytic amount of acid if required. Oxidation of an imine formed by reaction of diamine (9) with an appropriate aldehyde using oxidants such as Cu (II), nitrobenzene, or 2,3-dichloro- 5,6-dicyano-1,4-benzoquinone (DDQ) also affords heterocycles (10). Aminoamides (11, W=H) or diamides (11, W=R⁶CO) can be converted to fused imidazoles (10) by heating neat, or at an elevated temperature in a solvent such as xylene under acidic or neutral conditions.

Halogenation of the imidazo[4,5-b]pyridine ring at the 6-position can be accomplished using $Br_2$, or N-bromosuccinimide. Halogenation of the 7-position can be accomplished by reaction of the corresponding imidazopyridine-4-oxide (prepared by reaction of the imidazopyridine with peracids such as m-chloroperbenzoic acid) with $POCl_3$. When the 7-position is substituted other than hydrogen halogenation at the 5-position of the 4(N)-oxide precursor occurs on treatment with $POCl_3$. Chlorides may be substituted by bromides or iodides by treatment with either HBr or HI, respectively, in a solvent such as HOAc.

2-Alkyl-imidazo[4,5-b]pyridines can be substituted at the 5, 6, or 7 positions by displacement of a halogen at that position by nucleophiles such as cyanide (followed by hydrolysis to obtain carboxylic acids), amines, copper alkoxides, trialkylphosphites, and thiolates. Also, substitution of the halogens, in particular bromides or iodides, can be accomplished by reaction with a coupling partner such as alkylzinc or arylzinc halides, or monoalkylarylphosphonites in the presence of an appropriate metal catalyst such as nickel, palladium, ruthenium, or platinum. In cases where the displacement of a halogen is sluggish or otherwise complicated due to an acidic proton, the imidazopyridine may be protected at the 1, 3, or 4 positions by benzyl or other arylmethyl groups.

7-Methyl-2-propylimidazo[4,5-b]pyridine-5-carboxylic acid or the 2-ethyl analog is prepared from 7-methyl-2-propylimidazo[4,5-b]pyridine or the 2-ethyl analog by treatment with m-cloroperoxybenzoic acid to obtain the N-oxide which is then treated with $POCl_3$ to give 5-chloro-7-methyl-2-proplimidazo[4,5-b]pyridine or 2-ethyl analog. The chloride is then exchanged for a bromide by reaction of 5-chloro-7-methyl-2-propylimidazo[4,5-b]pyridine or the 2-ethyl analog with HBr in acetic acid. The resulting 5-bromo-07-methyl-2-propylimidazo[4,5-b]pyridine or 2-ethyl analog is treated with NaH in DMF followed by benzylbromide to obtain 3-benzyl-5-bromo-7-methyl-2-pyropylimidazo[4,5-b]Pyridine or its corresponding 2-ethyl analog which is in turn treated with CuCN in hot pyridine to obtain 3-benzyl-5-cyano-7-methyl-2-propylimidazo[4,5-b]pyridine or the corresponding 2-ethyl analog. The cyano compound is hydrolyzed to 3-benzyl-7-methyl-2-propylimidazo[4,5-b]pyridine-5-carboxylic acid or the corresponding 2-ethyl analog by treatment with $H_2SO_4$-$H_2O$. This acid is esterified by reaction with MeOH-HCl. The benzyl group is removed by hydrogenation at 1 atm. in MeOH-HCl solution using $Pd(OH)_2$ as catalyst. This compound can be alkylated as described earlier and the product methyl ester is can be converted to the carboxylic acid by treatment with hydroxide.

As shown in Reaction Scheme I-7, methods of preparing heterocycles of types (12 and 13) involve treatment of diamines (9) with reagents such as urea, phosgene, potassium cyanate, alkyl chloroformates, dialkylcarbonate, or carbon disulfide in the presence of bases such as potassium hydroxide or potassium carbonate. Amino acids (14) or (15) can be converted to (13) via Curtius or Hoffman Rearrangement on suitable derivatives such as acyl azides, hydroxyamides, or N-haloamides. Bicyclic compounds of type (16, E=sulfur or oxygen) are formed from 12 by reaction under neutral or basic conditions with alkyl halides, alkylmesdylates, alkyltosylates, trialkyloxonium salts, or with an appropriate diazoalkane. Compounds of type (16; E=oxygen or sulfur) are prepared by displacement reactions using alkoxides or alkyl mecaptides with chloro intermediates as indicated.

Diamines of type 9 can be prepared by a wide variety of methods such as hydrolysis of bis-amides or amino amides, reduction of dinitro or aminonitro or hydrazino or azido groups, displacement of heteroaromatic halides or alkoxy or thio or alkylthio or hydroxy or alkyl sulfonyl groups with ammonia or amines, or rearrangement of acyl azides or amides or acids (Curtius, Hoffman, or Schmidt rearrangements). [A. S. Tomcufcik, L. N. Starker in "Heterocyclic Compounds, Pyridine and Its Derivatives" Pt 3, E. Klingsberg Ed., Wiley Interscience, 1962, pp 59-62, and references cited there in; T. Nakagome in "Heterocyclic Compounds, Pyridazines" Vol. 28, R. N. Castle, Ed., Wiley Interscience, 1973, pp 597-601, and references cited therein; "Heterocyclic Compounds, The Pyrimidines" Vol. 16, D. J. Brown Ed., Wiley Interscience 1985, pp 299-325; E. Schipper, and A. R. Day *J. Am. Chem. Soc.* (1952) 74, 350; "Comprehensive Heterocyclic Chemistry," Vol. 5, A. R. Katritsky and C. W. Rees Eds., Pergamon Press 1984; pp 567-597 and 631-656 and references cited therein].

In cases wherein heterocycles of type 10 or 16 are not easily prepared from their corresponding diamines, or when these diamines cannot be prepared then alternative routes, involving fusion of the six member heterocycle onto an appropriately substituted imidazole, are used. Two of these routes are illustrated in Reaction Scheme I-8. For example, imidazo[4,5-d][1,2,3]triazines (18) are preferentially prepared by treatment of amino carboxamido imidazoles (17) with sodium nitrite in aqueous acid. Precursor imidazoles (17) are prepared by degradation of an appropriately substituted xanthine or by cndesnation of an appropriate imidate ester with aminocyanoacetamide. imidazo[4,5-b]pyridazines (20) can be prepared from imidazodicarboxylate esters (19) by treatment with hydrazine. Oxidation of (20) gives pyridazindiones (21). The oxygen(s) in (20) or (21) can be converted to other functionalities sich as halids or thiones, which are themselves precursors for the synthesis of more elaborate systems ["Comprehensive Heterocyclic Chemistry," Vol. 5, A. R. Katritsky and C. W. Rees Eds., Pergamon Press 1984; pp 567-597 and 631-656 and references cited therein].

SCHEME I-6

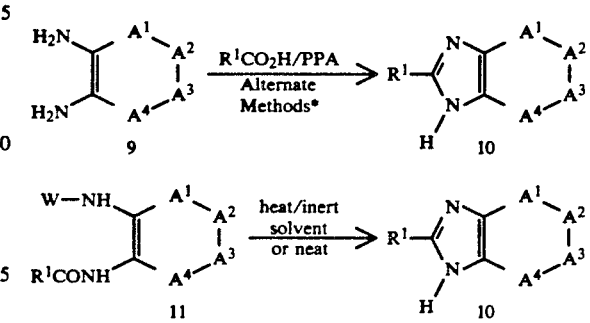

*Alternate reagents and reaction conditions:

SCHEME I-6 (-continued)

$R^1$—CN, PPA $R^1$—C(=NH·HCl)—(OC$_2$H$_5$), C$_2$H$_5$OH, Δ

$R^1$C(OCH$_3$)$_3$, toluene, H$^+$, Δ
$R^1$CHO, C$_2$H$_5$OH, Cu(OCH$_3$)$_2$

SCHEME I-7

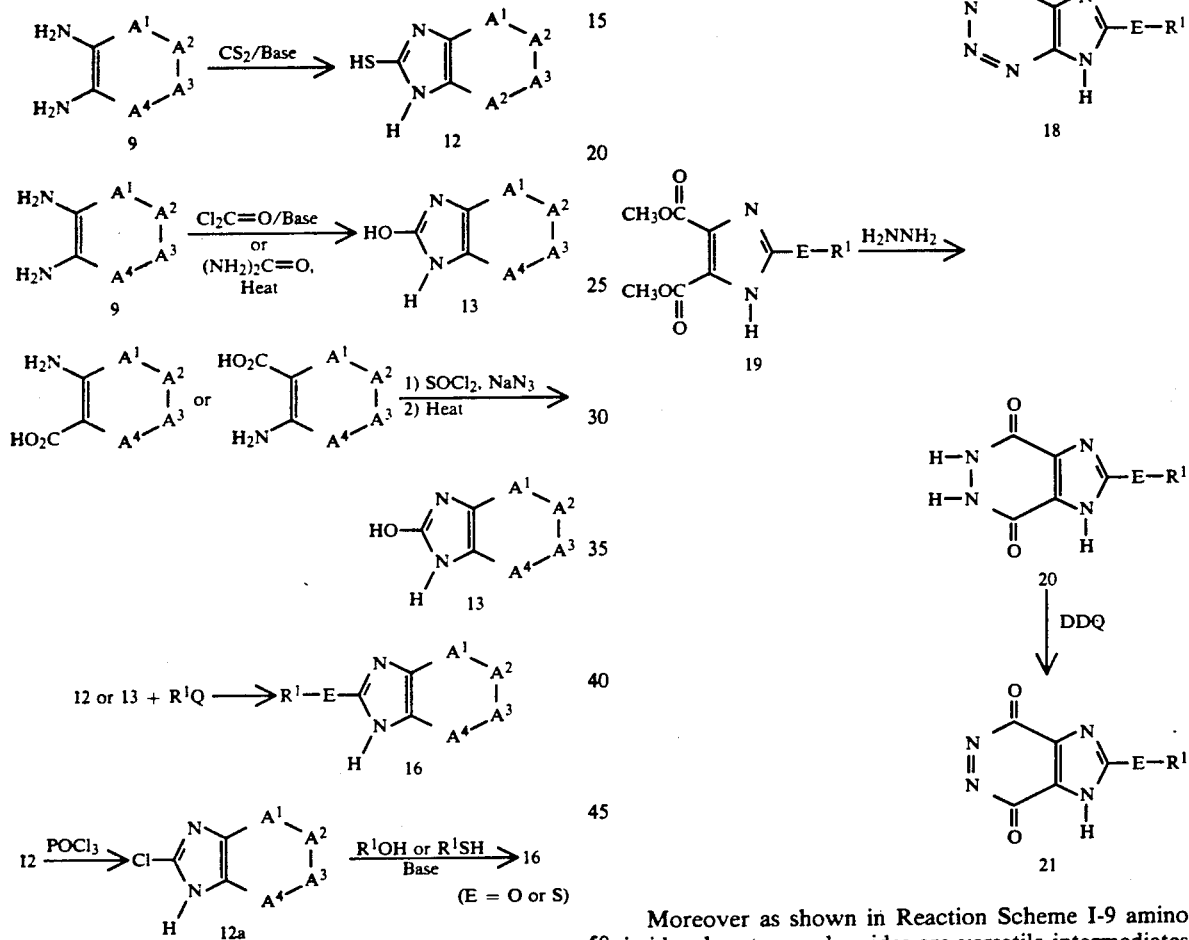

SCHEME I-8

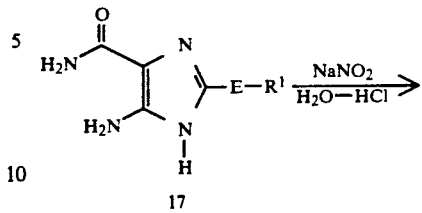

Moreover as shown in Reaction Scheme I-9 amino imidazole esters and amides are versatile intermediates for the preparation of purines. This scheme also illustrates the synthesis of the 6-membered heterocyclic ring after the alkylating agent 2 has been reacted with a suitably substituted imidazole to afford 22 or 24.

REACTION SCHEME I-9

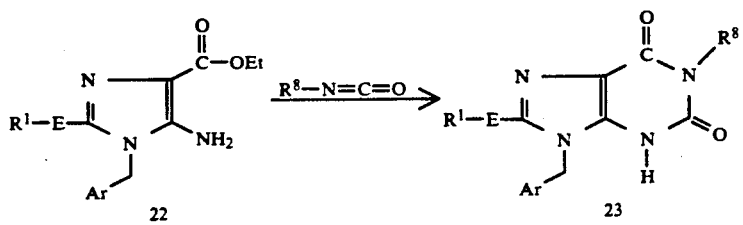

REACTION SCHEME I-9
-continued

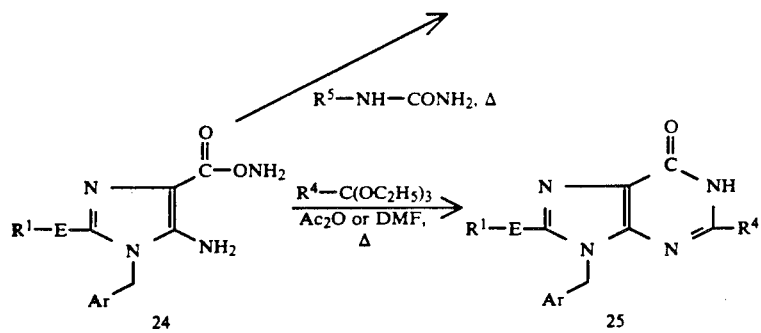

The preparation of reduced forms of heterocycles can be achieved by catalytic reduction, or by synthesis from a suitable imidazole precursor. For example, histidine and derivatives thereof react with formaldehyde to afford partially saturated imidazo[(4,5-c)]pyridines [cf. Neuberger, A. Biochem. J., (1944), 38, 309].

PART II: Preparation of nitrogen containing phenyl derivatives and coupling to the heterocycle described in Part II Alkylating agents of type 2a, where $Z^1$ represents a precursor or a protected form of Z, can be prepared by treatment of tolyl derivatives of type 1 under reaction conditions such as N-bromosuccinimide in the presence of a radical initiator such as dibenzoylperoxide (DBPO) or azo-bix-isobutyrylnitrile (AIBN). Alternatively, alcohols of type 3 can be converted to alkylating agents of type 2b by treatment with activating agents such as methanesulfonyl chloride (MsCl) or p-toluenesulfonyl chloride (TsCl), as described in Scheme II-1.

Tolyl derivatives of type 1 can be prepared by coupling heteroaryl halides of triflates (OTf) of type 5 with aryl zinc, magnesium, trialkyltin, boronic acids, or boronic esters of type 5 in the presence of catalysts such as bistriphenylphosphine nickel chloride or tetrakistriphenylphosphine palladium in solvents such as THF, or DMF. Alternatively, heteroaryl zinc, magnesium, trialkyltin, boron acids, or boronic esters of type 6 can be coupled to aryl halides or triflates of type 7 in the above manner, see Scheme II-2.

SCHEME II-1

SCHEME II-2

SCHEME II-2

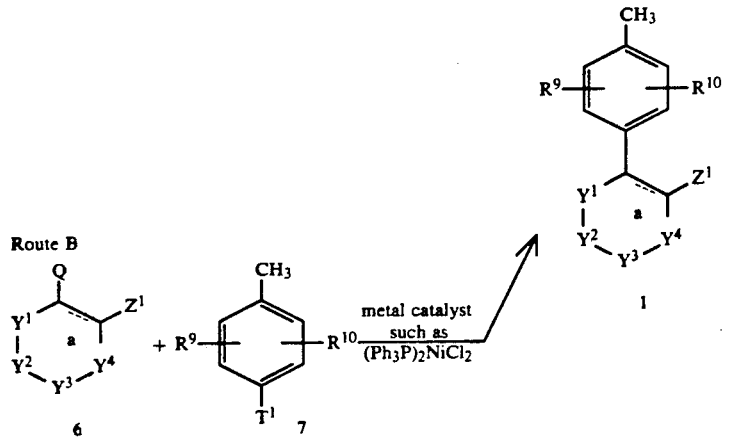

$T^1$ = halide or OTf
$Z^1$ = precursor or protected form of Z
Q = MgBr, ZnCl$_2$, Sn(CH$_3$)$_3$, B(OH)$_2$ or B(OR)$_2$, where R is lower alkyl
a = single or double bond The group $Z^1$ of type 1 compounds can be further manipulated, as shown in Schemes II-3 and II-4, after biaryl coupling. Nitriles 8 can be converted into carboxylic acids 9 which in turn may undergo a Curtius rearrangement giving amines 10. Amines 10 may be converted to sulphonamides 11 or diazotized and reacted with SO$_2$ in the presence of CuCl to give intermediate sulfonyl chlorides 12 which in turn are reacted with with amines such as tert-butyl amine to give 13. Sulfonamides 11 and 13 can be converted into alkylating agents as described in Scheme II-1 and coupled to the appropriate heterocycle to give sulfonamide 14. Compounds of type 14 are then treated with trifluoroacetic acid then acylated to give acylsulphonamides 15.

SCHEME II-3

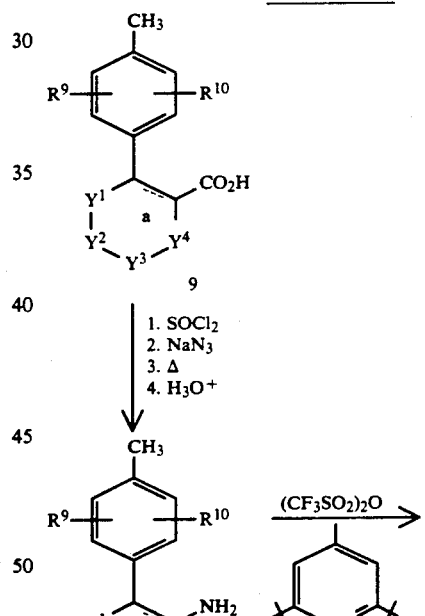

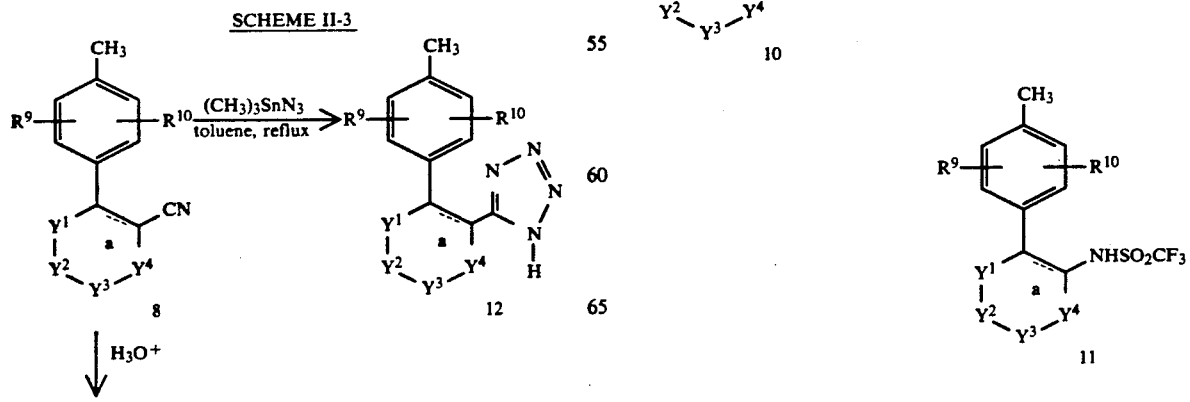

SCHEME II-4

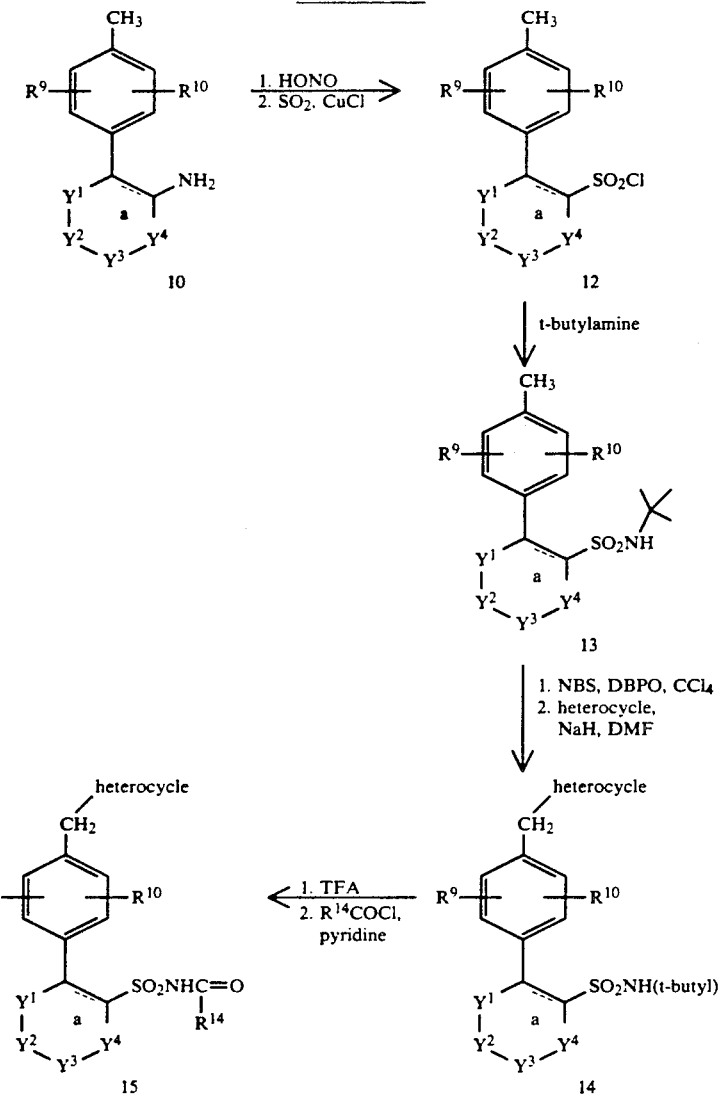

Scheme II-5 describes an alternative route from those described in Scheme II-2 for the preparation of tolyl derivatives of type 1, as well as exemplifying a route generally described in Scheme II-2. The coupling of the aryl and heteroaryl portions can be accomplished as exemplified by the preparation of 17 by reaction of pyridine 16 with phenyl chloroformate and p-tolylmagnesium bromide 17 in the presence of CuI, followed by aromatization of the dihydropyridine intermediate 18 with hot sulfur, to give the tolyl derivative 21. Alternatively, 4-bromotoluene 19, upon treatment with butyllithium and zinc chloride to generate the tolylzinc intermediate, which in the presence of a nickel catalyst and heteroaryl halide 20 gives the total derivative 21.

Illustrative of one technique for the preparation of compounds of Formula I from alkylating agents of type 2a and 2b is the conversion of 21 to bromide 22, shown in Scheme II-5, followed by alkylation with heterocycle 23. Alkylation is typically accomplished by treatment of the heterocycle with sodium hydride in DMF to give the sodium salt exemplified by 24, which upon treatment with bromide 22 gives the cyano compound 25, as shown in Scheme II-6. Conversion of 25 to the tetrazole containing angiotensin II antagonist 26 is accomplished by reaction with trimethylstannyl azide, as shown in Scheme II-7.

SCHEME II-5

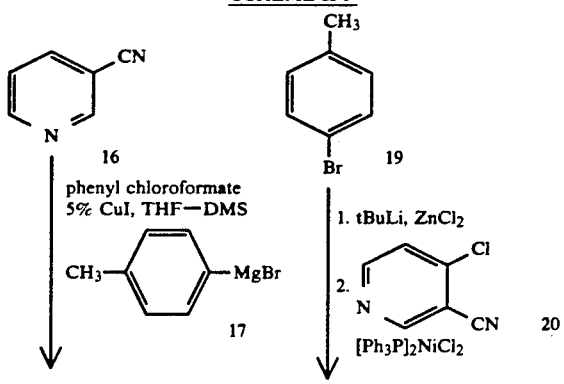

SCHEME II-5

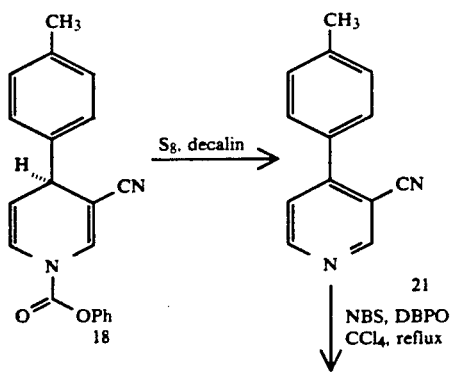

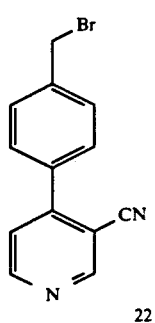

SCHEME II-6

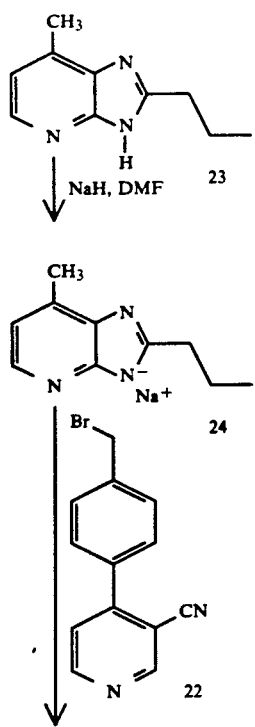

-continued
SCHEME II-6

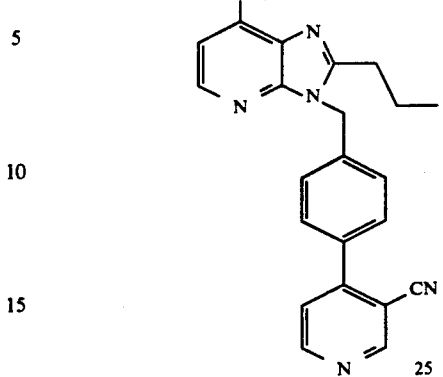

SCHEME II-7

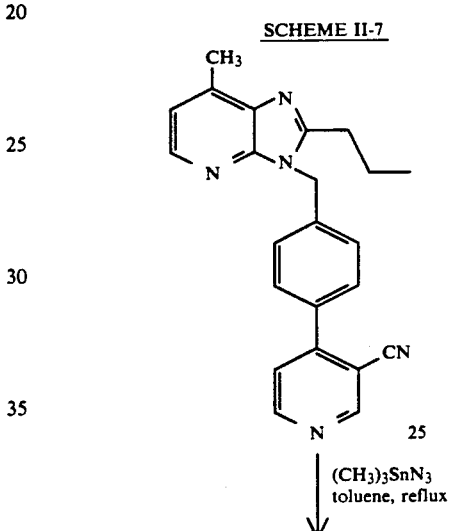

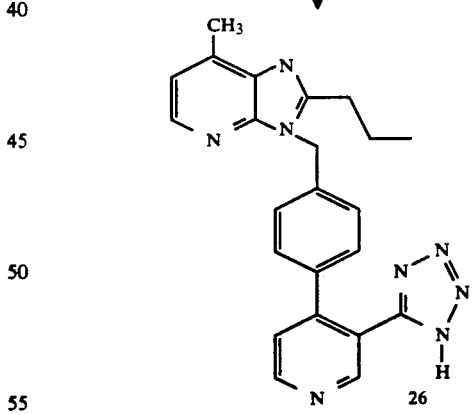

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 mL) homogenized, and then centrifuged. The mixture was filtered through a cheesecloth and the supernatant was centrifuged for 30 minutes at 20,000 rpm at 4° C. The pellet thus obtained was resuspended in 30 mL of 50 mM Tris-5 mM $MgCl_2$ buffer containing 0.2% Bovine Serum Albumin and 0.2 mg/mL Bacitracin and the suspension was used for 100 assay tubes. Samples tested for screening were done in duplicate. To the membrane preparation (0.25 mL) there was added $^{125}$I-Sar$^1$Ile$^8$-angiotensin II [obtained from New England Nuclear] (10 mL; 20,000 cpm) with or without the test sample and the mixture was incubated at 37° C. for 90 minutes. The mixture was then diluted with ice-cold 50 mM Tris-0.9% NaCl, pH 7.4 (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighted tissue (0.1 g is needed for 100 assay tubes) was suspended in Tris HCl (50 mM), pH 7.7 buffer and homogenized. The homogenate was centrifuged at 20,000 rpm for 15 minutes. Supernatant was discarded and pellets resuspended in buffer [Na$_2$HPO$_4$ (10 mM)-NaCl (120 nM)-disodium EDTA (5 mM) containing phenylmethane sulfonyl fluoride (PMSF) (0.1 mM)]. (For screening of compounds, generally duplicates of tubes are used). To the membrane preparation (0.5 mL) there was added $^3$H-angiotensin II (50 mM) (10 mL) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration (IC$_{50}$) of potential AII antagonist which gives 50% displacement of the total specifically bound $^3$H-antiogensin II was presented as a measure of the efficacy of such compounds as AII antagonists.

The potential antihypertensive effects of the compounds described in the present invention may be evaluated using the methodology described below: Male Charles River Sprague-Dawley rats (300-375 gm) were anesthetized with methohexital (Brevital; 50 mg/kg i.p.) and the trachea was cannulated with PE 205 tubing. A stainless steel pitching rod (1.5 mm thick, 150 mm long) was inserted into the orbit of the right eye and down the spinal column. The rats were immediately placed on a Harvard Rodent Ventilator (rate-60 strokes per minute, volume—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperatures probe. Atropine (1 mg/kg i.v.) was then administered, and 15 minutes later propanolol (1 mg/kg i.v.). Thirty minutes later angiotensin II or other agonists were administered intravenously at 30 minute intervals and the increase in the diastolic blood pressure was recorded before and after drug or vehicle administration.

Using the methodology described above, representative compounds of the invention were evaluated and found to exhibit an activity of at least IC$_{50}$<50 mM thereby demonstrating and confirming the utility of the compounds of the invention as effective AII antagonists.

Receptor assay using rat brain membrane preparation

Membranes from rat brain (thalamus, hypothamus and midbrain) were prepared by homogenization in 50 mM Tris HCl (pH 7.4), and centrifuged at 50,000 x g. The resulting pellets were washed twice in 100 mM NaCl, 5 mM Na$_2$·EDTA, 10 mM Na$_2$HPO$_4$ (pH 7.4) and 0.1 mM PMSF by resuspension and centrifugation. For binding assays, the pellets were resuspended in 160 volumes of binding assay buffer (100 mM NaCl, 10 mM Na$_2$HPO$_4$, 5 mM Na$_2$·EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$ Ile$^8$-angiotensin II (1 μM) (for nonspecific binding) or test compounds (for displacement) and 10 μl of [$^{125}$I]Sar$^1$-Ile$^8$-angiotensin II (23-46 pM) were added to duplicate tubes. The receptor membrane preparation (500 μl) was added to each tube to initiate the binding reaction. The reaction mixtures were incubated at 37° C. for 90 minutes. The reaction was then terminated by filtration under reduced pressure through glass-fiber GF/B filters and washed immediately 4 times with 4 ml of 5 mM ice-cold Tris HCl (pH 7.6) containing 0.15 M NaCl. The radioactivity trapped on the filters was counted using a gamma counter.

Thus, the compounds of the invention are useful in treating hypertension. They are also of value in the management of acute and chronic congestive heart failure. These compounds may also be expected to be useful in the treatment of secondary hyperaldeosteronism, primary and secondary pumonary hyperaldeosteronism, primary and secondary pulmonary hypertension, renal failure such as diabetic nephropathy, glomerulonephritis, slceroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atheroslecerotic process. The application of the compounds of this invention for these and similar disorders will be apparent to those skilled in the art.

The compounds of this invention are also useful to treat elevated intraocular pressure and to enhance retinal blood flow and can adminsitered to patients in need of such treatment with typical pharmaceutical formulations such as tablets, capsules, injectable and the like as well as topical ocular formulations in the form of solutions, ointments, insets, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, supportories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, crypenamine acetates and cryptenamine tannates, deserpidine, diazoxide, guanethidine sulfate, hydralazine hydrochloride, hydrochlorothiazide, metolazone, metoprolol tartate, methylclothiazide, methyldopa, methyldopate hydrochloride, minoxidil, pargyline hydrochloride, polythiazide, prazosin, propanolol, *rauwolfia serpentina*, rescinnamine, reserpin, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enealapril, enalaprilat, fosinopril sodium, lisinoporil, pentopril, quinapril hydrochloride, ramapril, teprotide, zofenopril calcium, diflunisal, diltriazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range: hydrochlorothiazide (15–200 mg) chlorothiazide (125–2000 mg), ehtyacrynic acid (15–200 mg), amiloride, (5–20 mg), furosemide (5–80 mg), propanolol (20–480 mg), timolol maleate (5–60 mg.), methyldopa (65–2000 mg), felodipine (5–60 mg), nifedipine (5–60 mg), and nitrendipine)5–60 mg). In addition, triple drug combinations of hydrochlorothiazide (15–200 mg) plus amiloride (5–20 mg) plus angiotensin II antagonist of this invention (3–200 mg) or hydrochlorothiazide (15–200 mg) plus timolol maleate (5–60) plus an angiotensin II antagonist of this invention (0.5–250 mg) or hydrochlorothiazide (15–200 mg) and nifedipine (5–60 mg) plus anangiotensin II antagonist of this invention (0.5–250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit, For instance, tablets may be coated with shellac, sugar or both. A syrup or elixir may contain the active compound, sucrose as a sweetening, agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vacular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an dependent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, an nootropic agents such as piracetam.

In order to achieve optimal anxiolytic activity, the compounds of this invention may be combined with other anxiolytic agents such as alprazolam, lorazepam, diazepam, and buspirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of Formula I and their incorporation into pharmaceutical compositions and as such are not to be considered nor construed as limiting the invention set forth in the claims appended thereto.

EXAMPLE 1

7-Methyl-2-propyl-3-[[4-[3-(1H-tetrazol-5-yl)-4-pyridinyl]phenyl]methyl]imidazo[4,5-b]pyridine.

Step A: Preparation of 2,3-diamino-4-picoline (cf. Lappin, G. R.; Slezak, F. B. J. Am. Chem. Soc., 1950, 72,2806–7)

To a slurry of 2-amino-4-methyl-3-nitropyridine (10.0 g, 65.3 mmol) in 350 ml of 95% EtOH was added 500 mg of a 10% Pd/C catalyst. The mixture was stirred under a $H_2$ atmosphere (1 atm) for 36 hours. Filtration and evaporation gave a black solid which was used directly in the next step.

Step B: Preparation of 7-methyl-2-propylimidazo [4,5-b]pyridine (cf. Lappin, G. R.; Slezak, F. B. J. Am. Chem. Soc., 1950, 72, 2806–7)

A mixture of butyric acid (6.57 mL, 71.9 mmol), 2,3-diamino-4-picoline (8.05 g, 65.4 mmol), and polyphosphoric acid (50 g) was heated to 100° C. with stirring for 3 hours, and monitored by tlc of $NH_4OH$ neutralized aliquots. Basification ($NH_4OH$), extraction ($CH_2Cl_2$, 4×50 mL), drying ($K_2CO_3$), purification (by filtering through 100 g silica gel, EtOAc elution), and concentration gave the title compound as an amorphous tan solid which was judged pure by $^1H$ NMR and tlc: mp 110°–112° C. (without recrystallization).

$^1H$ NMR (300 MHz, $CDCl_3$, ppm): δ8.13 (d, 1H, J=5 Hz), 7.01 (d, 1H, J=5 Hz), 3.01 (t, 2H, J=7.8 Hz), 2.67 (s, 3H), 2.07-1.93 (m, 2H), 1.06 (t, 3H, J=7.5 Hz).

Step C: 3-Cyano-4-(4-tolyl)pyridine

To a stirred mixture of 3-cyanopyridine (10 g, 96 mmol), CuI (914 mg, 4.8 mmol), p-tolylmagnesium bromide (100 mL of a 1M solution in $Et_2O$, 100 mmol), THF (200 mL), and $Me_2S$ (100 mL) under $N_2$ at 23° C. was added phenyl chloroformate (12.6 mL, 100 mmol) over a 30 min. period. After 2 h, aqueous $NH_4Cl$ (20%, 100 mL) and $Et_2O$ (100 mL) were added and the mixture was warmed to room temperature. The organic layer was washed sequentially with 1N HCl (50 mL), $H_2O$ (50 mL), a 1:1 mixture of 20% aqueous $NH_4Cl$ and conc. $NH_4OH$ (3×50 mL), and brine (50 mL) then dried ($MgSO_4$). Concentration gave the crude 3-cyano-1-phenoxycarbonyl-4-(p-tolyl)-1,4-dihydropyridine as a tan solid. A portion (8 g) of this crude dihydropyridine was treated with $S_8$ (810 mg) in decalin (25 mL) at reflux for 6 h. This reaction was cooled to rt, EtOAc (100 mL) and $H_2O$ (50 mL) were added and the resulting mixture was filtered through celite ®. The organic layer was washed sequentially with 1 N NaOH (30 mL), water and brine then dried over ($K_2CO_3$). Purification (flash chromatography, 20% EtOAc/hexanes) gave the titled compound as a tan solid.

$^1H$ NMR (300 MHz, $CDCl_3$) δ8.91 (s, 1H), 8.76 (d, 1H, J=4.5 Hz), 7.52 (d, 2H, J=8 Hz), 7.44 (d, 1H, J=4.5 Hz), 7.33 (d, 2H, J=8 Hz).

Step D: 3-Cyano-4-(4-bromomethylphenyl)pyridine

A solution of 3-cyano-4-(4-tolyl)pyrifine (485 mg, 2.66 mmol), N-bromosuccinimide (929 mg, 5.22 mmol), and dibenzoylperoxide (64 mg, 0.266 mmol) in $CCl_4$ (15 mL) was heated to reflux for 6 h. The mixture was cooled and water (50 mL) and $CH_2Cl_2$ (30 mL) were added. The organic layer was dried ($MgSO_4$) and purified by flash chromoatography (10% EtOAc/hexanes). The product is not kept in concentrated form for more than 5 minutes and stored only in $CH_2Cl_2$ at 0° C. to minimize polymerization.

Step E: 7-methyl-2-propyl-3-[[4-(3-cyanopyridin-4-yl)phenyl]methyl]imidazo[4,5-b]pyridine.

To a solution of 7-methyl-2-propylimidazo[4,5-b]pyridine (170 mg, 1.0 mmol) from Step B in DMF at rt was added NaH (1.0 mmol). After 20 min, 3-cyano-4-(4-bromomethylphenyl)pyridine (1 mL of a 2M solution in $CH_2Cl_2$, 2 mmol) was added and the mixture was stirred at rt for 3 h. HOAc (100 μL) was added, the excess DMF was removed in vacuo then the crude product was isolated by extraction with EtOAc from brine. Purification by flash chromatography (100% EtOAc) gave the above titled compound as a glassy solid.

$^1H$ NMR (300 MHz, $CDCl_3$) δ8.91 (s, 1H), 8.76 (d, 1H, J=5 Hz), 8.18 (d, 1H, J=5 Hz), 7.53 (d, 2H, J=8 Hz), 7.39 (d, 1H, J=5 Hz), 7.27 (d, 2H, J=8 Hz), 7.02 (d, 1H, J=5 Hz), 5.49 (s, 2H), 2.84 (dd, 2H), 2.67 (s, 3H), 1.86-1.74 (m, 2H), 0.98 (t, 3H).

Step F: 7-Methyl-2-propyl-3-[[4-[3-(1H-tetrazol-5-yl)-4-pyridinyl]phenyl]methyl]imidazo[4,5-b]pyridine.

A solution of 7-methyl-2-propyl-3-[[4-(3-cyanopyridin-4-yl)phenyl]methyl]imidazo[4,5-b]pyridine (50 mg, 0.136 mmol) and trimethylstannylazide (84 mg, 0.408 mmol) in toluene (4 mL) was heated to reflux for 4 days. The mixture was cooled to rt, concentrated, then purified by flash chromatography on $SiO_2$ (80/20/1 $CH_2Cl_2$/MeOH/$NH_4OH$) to give the product as a white solid.

$^1H$ NMR (300 MHz, $CD_3OD$) δ8.74 (s, 1H), 8.68 (d, 1H), 8.17 (d, 1H, J=5 Hz), 7.54 (d, 1H, J=5 Hz), 7.18–7.60 (m, 5H), 5.58 (s, 2H), 2.85 (dd, 2H), 2.65 (s, 3H), 1.80–1.61 (m, 2H), 0.96 (t, 3H).

EXAMPLE 2

5,7-Dimethyl-2-ethyl-3-[[4-(3-1H-tetrazol-5yl)-4-pyridinyl]phenyl]methyl]imidazo[4,5-b]pyridine Step A: Preparation of 2-nitroamino-4,6-dimethylpyridine 2-Amino-4,6-dimethylpyridine (10.0 g, 81.8 mmol) was added portion-wise to 65 mL of $H_2SO_4$ (conc. d=1.84) which was stirred (mechanical) at 0° C. After complete addition, the mixture was warmed to room temperature until the mixture became homogeneous. The solution was then cooled to −10° C. and a pre-cooled (0° C.) mixture of conc $HNO_3$ (11.5 mL, d=1.40) and $H_2SO_4$ (8.2 mL, d=1.84) was added at such a rate as not to raise the internal reaction temperature above −9° C. Ten minutes after the addition was complete this cooled (−10° C.) mixture was poured onto 400 g of crushed ice. The resulting slurry was neutralized by the addition of conc $NH_4OH$ (to pH 5.5) while cooling (ice bath). The solid was isolated by filtration, and dried at room temperature to give the title compound as a white solid.

Step B: Preparation of 2-amino-3-nitro-4,6-dimethylpyridine

To 75 mL of stirred conc $H_2SO_4$ cooled to −5° C. (ice-salt bath) was added 4,6-dimethyl-2-nitroaminopyridine (13.2 g, 79 mmol) portion-wise at such a rate as to maintain the internal temperature below −3° C. The mixture was warmed to 0° C. until homogeneous (30 minutes) at which time tlc ($SiO_2$, 1:1 EtOAc/hexanes on a $NH_4OH$ neutralized aliquot) indicated that the rearrangement was complete. The mixture was poured onto 400 g of crushed ice and the pH was adjusted to 5.5 by the addition of conc $NH_2OH$. The resulting yellow slurry was cooled to 0° C., filtered, washed with cold water (50 mL), and dried at room temperature to give a mixture of the title compound and the 5-nitro isomer in a 55:45 ratio (determined by $^1H$ NMR). This mixture was used directly in the next step.

Step C: Preparation of 5,7-dimethyl-2-ethylimidazo[4,5-b]pyridine

To a mixture of 8.44 g of a 55:45 mixture of 2-amino-3-nitro-4,6-dimethylpyridine and 2-amino-5-nitro-4,6-dimethylpyridine in MeOH (1.2 L) was added 10% Pd/C (2.4 g). The reaction vessel was evacuated then purged with $H_2$ at 1 atm. and stirred vigorously for 18 h. Filtration through a celite pad, and concentration gave 6.65 g of a mixture of 2,3-diamino-4,6-dimethylpyridine and 2,5-diamino-4,6-dimethylpyridine as a dark solid. To 5.40 g (39.4 mmol) of this mixture was added propionic acid (8.80 mL, 118 mmol) followed by polyphosphoric acid (100 mL). This stirred mixture was heated to 90° C. for 3 h then to 100° C. for 1 hour. The inside walls of the flask were scraped with a spatula to assist dissolution of the solids. After the reaction was complete, the warm mixture was poured onto 300 g of ice and the mixture was made basic with $NH_4OH$. The mixture was extracted (4×50 mL $CH_2Cl_2$), dried ($K_2CO_3$) and concentrated to give a mixture of the title compound and 4,6-dimethyl-2,5-bis(propionamido)pyridine. Purification ($SiO_2$, 5% MeOH/ EtOAc) gave the title compound as the slower eluting component.

$^1H$ NMR ($CD_3OD$, 300 MHz), ppm): δ6.95 (s, 1H), 2.92 (q, J=7.8 Hz, 2H), 2.54 (apparent s, 6H), 1.40 (t, J=7.8 Hz, 3H).

EXAMPLE 3

5-Carbomethoxy-2-ethyl-7-methyl-3-[[4-(3-(1H-tetrazol-5-yl)-4-pyridinyl]phenyl]methyl]imidazo[4,5-b]pyridine Step A: Preparation of 2-ethyl-7-methylimidazo[4,5-b]pyridine-4-oxide A solution of 28 g (174 mmol) of 2-ethyl-7-methylimidazo[4,5-b]pyridine (prepared according to Example 1, Steps A and B, but substituting propionic acid in place of butyric acid in Step B) and m-chloroperbenzoic acid (80–90%, 44.6 g) in $CHCl_3$ (300 mL) was heated at reflux for 0.5 hours. The mixture was concentrated and purified ($SiO_2$, 100% $CH_2Cl_2$ gradient to 30% $CH_2Cl_2$/MeOH) to give the title compound as a solid.

$^1H$ NMR (300 MHz, $CD_3OD$, ppm): δ8.13 (d, 1H, J=6 Hz), 7.13 (d, 1H, J=6 Hz), 3.01 (q, 2H, J=7.5 Hz), 2.60 (s, 3H), 1.46 (t, 3H, J=7.5 Hz).

Step B: Preparation of 5-chloro-2-ethyl-7-methylimidazo[4,5-b]pyridine

A mixture of 29.75 g (0.168 mol) of the product of Step A, $CHCl_3$ (25 mL) and $POCl_3$ (160 mL) was heated to 80° C. for 1 hour. After pouring over ice, the mixture was neutralized by careful addition of $NH_4OH$ and extracted with EtOAc. Concentration gave the title compound as a solid.

$^1H$ NMR (250 MHz, $CDCl_3$, ppm): δ7.07 (s, 1H) 3.10 (q, 2H, J=7.5 Hz), 2.67 (s, 3H), 1.48 (t, 3H, J=7.5 Hz).

Step C: Preparation of 5-bromo-2-ethyl-7-methylimidazo[4,5-b]pyridine

A mixture of 22.2 g (0.113 mol) of the product of Step B in 30% HBr-HOAc was heated to 100° C. for 19 hours. The mixture was poured onto ice, neutralized with $NH_4OH$, extracted (5×EtOAc), and the organic layers were concentrated to give the title compound as a solid after crystallization from EtOAc.

$^1H$ NMR (300 MHz, $CDCl_3$, ppm): δ7.22 (s, 1H) 3.13 (q, 2H, J=7.5 Hz), 2.66 (s, 3H), 1.47 (t, 3H, J=7.5 Hz).

Step D: Preparation of 3-benzyl-5-bromo-2-ethyl-7-methylimidazo[4,5-b]pyridine

To a solution of 10 g (39 mmol) of the product of Step C in DMF (70 mL) at rt was added NaH (1.3 g of an 80% oil dispersion, 43 mmol). After 20 minutes benzyl bromide (5.15 mL, 43 mmol) was added and the reaction was stirred for 16 hours. The mixture was poured onto 500 g of ice and the solid residue was filtered, washed with water and air dried to give the title compound.

$^1H$ NMR (300 MHz, $CDCl_3$, ppm): δ7.33–7.22 (m, 3H), 7.19 (s, 1 H), 7.11–7.07 (m, 2H), 5.42 (s, 2H), 2.76 (q, 2H, J=7.5 Hz), 2.63 (s, 3H), 1.29 (t, 3H, J=7.5 Hz).

Step E: Preparation of 3-benzyl-5-cyano-2-ethyl-7-methylimidazo[4,5-b]pyridine

A mixture of 620 mg (1.8 mmol) of the product of Step D and CuCN (806 mg, 9.0 mmol) was heated in pyridine (4 mL) at reflux for 10 hours under nitrogen. The reaction was cooled, then water (50mL), KCN (1.17g), and EtOAc (20 mL) were added and the mixture was heated to 50° C. for 5 min. Cooling and extraction with EtOAc (2×50 mL) gave the title compound as a tan solid.

$^1$H NMR (400 MHz, CDCl$_3$, ppm): δ7.40 (s, 1H), 7.35–7.20 (m, 3H), 7.18–7.07 (m, 2H), 5.44 (s, 2H), 2.83 (q, 2H, J=7.5 Hz), 2.67 (s, 3H), 1.32 (t, 3H, J=7.5 Hz).

Step F: Preparation of methyl 3-benzyl-2-ethyl-7-methylimidazo[4,5-b]pyridine-5-carboxylate A solution of 440 mg (1.59 mmol) of the product of Step E in H$_2$SO$_4$ (4 mL) and H$_2$O (4 mL) was heated to 80° C. for 8 hours. The reaction was cooled, MeOH (150 mL) was added, then conc NH$_4$OH was added until the mixture turned basic. The white solid (NH$_4$)$_2$SO$_4$ was filtered and washed with MeOH. The water and MeOH were removed in vacuo and and the residue was taken up in MeOH and then filtered to remove any remaining (NH$_4$)$_2$SO$_4$. After concentrating, and removal of water from the residue by evaporation from toluene, anhydrous 3% HCl-MeOH (50mL) was added and the mixture was stirred overnight at rt. Filtration, concentration, and extraction from 5% aqueous Na$_2$CO$_3$ with CH$_2$Cl$_2$ gave the crude title compound as a solid.

$^1$H NMR (300 MHz, CDCl$_3$, ppm): δ7.93 (s, 1H) 7.38–7.29 (m, 3H), 7.12–7.03 (m, 2H), 5.53 (s, 2H), 3.96 (s, 3H), 2.78 (q, 2H, J=7.5 Hz), 2.70 (s, 3H), 1.29 (t, 3H, J=7.5 Hz).

Step G: Preparation of methyl 2-ethyl-7-methylimidazo[4,5-b]pyridine-5-carboxylate A mixture of 750 mg of the crude product of Step F in MeOH (30 mL), concentration aqueous HCl (1 mL), and 100 mg of moist Pearlman's catalyst were shaken under 1 atm. H$_2$ for 24 hours. The reaction was incomplete so 100 mg more of the catalyst was added and the reaction was shaken as described above for an additional 24 hours. Filtration, concentration, and extraction from dilute NH$_4$OH with EtOAc followed by drying (Na$_2$SO$_4$), concentration, and purification (SiO$_2$, 5% MeOH/EtOAc) gave the title compound as a solid.

$^1$H NMR (400 MHz, CDCl$_3$, ppm): δ7.90 (s, 1H), 4.00 (s, 3H), 3.10 (q, 2H, J=7.5 Hz), 2.71 (s, 3H), 1.38 (t, 3H, J=7.5 Hz).

Step H: Preparation of 5-Carbomethoxy-2-ethyl-7-methyl-3-[[4-(3-1H-tetrazol-5-yl)-4-pyridinyl]phenyl]methyl]imidazo[4,5-b]pyridine Utilizing the procedures described in Example 1, Steps E and F the titled compound can be prepared.

EXAMPLE 4

5-Carbomethoxy-7-methyl-2-propyl-3-[[4-(3-(1H-tetrazol-5-yl)-4-pyridinyl]phenyl]methyl]imidazo[4,5-b]pyridine Following the procedures of Example 3 but substituting 7-methyl-2-propylimidazo[4,5-b]pyridine in place of 2-ethyl-7-methylimidazo[4,5-b]pyridine, in Step A of Example 3, the titled compound can be prepared.

EXAMPLE 5

7-Methyl-2-propyl-3-[4-[3-(1H-tetrazole-5-yl)-2-pyridinyl]phenyl]methylimidazo[4,5-b]pyridine-5-carboxylic acid The title compound can be prepared by treating 5-carbomethoxy-7-methyl-2-propyl-3-[[4-[3-(1H-tetrazole-5-yl)-2-pyridinyl]phenyl]methyl]imidazo[4,5-b]pyridine with 1 equivalent of NaOH in aqueous methanol at 20° C. for 24 hours followed by concentration.

EXAMPLE 6

2-Ethyl-7-methyl-3-[4-[3-(1H-tetrazole-5-yl)-2-pyridinyl]phenyl]methylimidazo[4,5-b]pyridine-5-carboxylic acid The title compound can be prepared by treating 2-ethyl-5-carbomethoxy-7-methyl-3-[[4-[3-(1H-tetrazole-5-yl)-2-pyridinyl]phenyl]methyl]imidazo[4,5-b]pyridine with 1 equivalent of NaOH in aqueous methanol at 20° C. for 24 hours followed by concentration.

EXAMPLE 7

7-Methyl-2-propyl-3-[[4-[2-(1H-tetrazol-5-yl)-3-pyridinyl]phenyl]methyl]imidazo[4,5-b]pyridine.

Step A: 2-Cyano-3-(4-tolyl)pyridine

To a mixture of p-tolylmagnesium bromide (9.3 mL of a 1M solution in Et$_2$O, 9.28 mmol) in THF (17 mL) at −78° C. was added ZnCl$_2$ (9.3 mL of a 1M solution in Et$_2$O, 9.28 mmol). The resulting slurry was warmed to rt for 20 min then cooled to 0° C. Bis-(triphenylphosphine)nickel(II) chloride (178 mg, 0.27 mmol) and 3-bromo-2-cyanopyridine (1.0 g, 5.5 mmol); (prepared as reported: Chem. Pharm. Bull., 1985, vol. 33, P. 565) were added in one portion. After 1 h, saturated aqueous NH$_4$Cl (50 mL) was added and the mixture was extracted with EtOAc (2×50 mL). Purification by flash chromatography (40% EtOAc/hexanes) gave the above titled compound as a white solid.

Step B: 2-Cyano-3-(4-bromomethylphenyl)pyridine

A mixture of 2-cyano-3-(4tolyl)pyridine (940 mg, 4.84 mmol), N-bromosuccinimide (1.03 mg, 5.81 mmol), and dibenzoylperoxide (117 mg, 0.48 mmol) in CCl$_4$ (70 mL) was heated to reflux to 2 h. The mixture was cooled then filtered through 50 g of silica gel eluting with CH$_2$Cl$_2$. The product was purified further by flash chromatography (20% EtOAc/hexanes) to give the above titled compound as a white solid.

$^1$H NMR (300 MHz, CDCl$_3$) δ8.71 (d, 1H), 7.86 (d, 1H), 7.64–7.55 (m, 5H), 4.56 (s, 2H).

Step C: 7-Methyl-2-propyl-3-[[4-(2-cyanopyridin-3-yl)phenyl]methyl]imidazo[4,5-b]pyridine To a solution of 7-Methyl-2-propylimidazo[4,5-b]pyridine (320 mg, 1.83 mmol) from Example 1 Step B in DMF (9 mL) at rt was added NaH (82 mg of an 80% dispersion in oil, 2.74 mmol). After 20 min., 2-cyano-3-(4-bromomethyl- phenyl)pyridine (600 mg, 2.19 mmol) was added and the mixture was stirred at rt for 3 h. Brine (100 mL) and aqueous NH$_4$Cl (40 mL) were added and the product was extracted with EtOAc. Purification by flash chromatography (100% EtOAc) gave the above titled compound.

$^1$H NMR (300 MHz, CDCl$_3$) δ8.65 (dd, 1H, J=4.8, 1.5 Hz), 8.18 (d, 1H, J=4.8 Hz), 7.77 (dd, 1H, J=8.1, 1.8 Hz), 7.56–7.45 (m, 3H), 7.25 (d, 2H, J=8.4 Hz), 7.01 (d, 1H, J=5.1 Hz) 5.54 (s, 2H), 2.81 (t, 2H, J=7.5 Hz), 2.67 (s, 3H), 1.88–1.70 (m, 2H), 0.98 (t, 3H, J=7.5 Hz).

Step D: 7-Methyl-2-propyl-3-[[4-[2-(1H-tetrazol-5-yl)-3-pyridinyl]phenyl]methyl]imidazo[4,5-b]pyridine.

A solution of 7-methyl-2-propyl-3-[[4-(2-cyanopyridin-3-yl)phenyl]methyl]imidazo[4,5-b]pyridine (300 mg, 0.817 mmol) and trimethylstannylazide (504mg, 2.45 mmol) in toluene (3 mL) was heated to reflux for 36 h. The mixture was cooled to rt, concentrated, then purified by flash chromatography on SiO$_2$ (80/20/1 CH$_2$Cl$_2$/MeOH/NH$_4$OH) to give 7-methyl-2-propyl-3-[[4-[2-(1H-tetrazol-5-yl)-3-pyridinyl]phenyl]methyl]imidazo [4,5-b]pyridine as a white solid.

¹H NMR (300 MHz, CD₃OD) δ8.59 (broad d, 1H), 8.16 (d, 1H, J=5.1 Hz), 7.89 (d, 1H, J=7.8 Hz), 7.59-7.49 (m, 1H), 7.18-7.00 (m, 5H), 5.52 (s, 2H), 2.83 (dd, 2H), 2.65 (s, 3H), 1.80-1.63 (m, 2H), 0.96 (t, 3H).

Utilizing the procedure setforth in Example 7, Steps A through D and substituting the appropriate heterocycle, as described in Examples 2 through 6, Examples 8 through 12 can be prepared.

EXAMPLE 8

5,7-Dimethyl-2-ethyl-3-[[4-(3-1H-tetrazol-5-yl)-3-pyridinyl]phenyl]methyl]imidazo[4,5-b]pyridine

EXAMPLE 9

5-Carbomethoxy-2-ethyl-7-methyl-3-[[4-(3-1H-tetrazol-5-yl)-3-pyridinyl]phenyl methyl]imidazo[4,5-b]pyridine

EXAMPLE 10

5-Carbomethoxy-7-methyl-2-propyl-3-[[4-(3-(1H-tetrazol-5-yl)-3-pyridinyl]phenyl]methyl]imidazo[4,5-b]-pyridine

EXAMPLE 11

5-Carboxy-7-methyl-2-propyl-3-[[4-(3-(1H-tetrazol-5-yl)-3-pyridinyl)]phenyl]methyl]imidazo[4,5-b]pyridine

EXAMPLE 12

5-Carboxy-2-ethyl-7-methyl-3-[[4-(3-1H-tetrazol-5-yl)-3-pyridinyl]phenyl]methyl]imidazo[4,5-b]pyridine

EXAMPLE 13

7-Methyl-2-propyl-3-[[4-[3-(1H-tetrazol-5-yl)-2-pyridinyl]phenyl]methyl]imidazo[4,5-b]pyridine.

The title compound was prepared according to the procedure described in Example 7 and substituting 2-chloro-3-cyanopyridine.

¹H NMR (300 MHz, CD₃OD) δ8.66 (dd, 1H, J=4.8, 1.8 Hz), 8.16 (d, 1H, J=4.8 Hz), 7.99 (dd, 1H, J=7.8, 1.5 Hz), 7.50 (dd, 1H, J=7.8, 5.1 Hz), 7.25 (d, 2H, J=8.1 Hz), 7.13 (d, 1H, J=4.8 Hz), 7.05 (d, 2H, J=8.1 Hz), 5.55 (s, 2H), 2.84 (t, 2H, J=7.5 Hz), 2.65 (s, 3H), 1.76-1.65 (m, 2H), 0.96 (t, 3H, J=7.5 Hz).

Utilizing the procedure setforth in Example 13 and substituting the appropriate heterocycle, as described in Examples 2-6, Examples 14 through 18 can be prepared.

EXAMPLE 14

5-Carboxy-7-methyl-2-propyl-3-[[4-(3-(1H-tetrazol-5-yl)-2-pyridinyl)]phenyl]methyl]imidazo[4,5-b]pyridine

EXAMPLE 15

5-Carboxy-2-ethyl-7-methyl-3-[[4-(3-1H-tetrazol-5-yl)-2-pyridinyl]phenyl]methyl]imidazo[4,5-b]pyridine

EXAMPLE 16

5,7-Dimethyl-2-ethyl-3-[[4-(3-1H-tetrazol-5-yl)-2-pyridinyl]phenyl]methyl]imidazo[4,5-b]pyridine

EXAMPLE 17

5-Carbomethoxy-2-ethyl-7-methyl-3-[[4-(3-H-tetrazol-5-yl)-2-pyridinyl]phenyl]methyl]imidazo[4,5-b]pyridine

EXAMPLE 18

5-Carbomethoxy-7-methyl-2-propyl-3-[[4-(3-(1H-tetrazol-5-yl)-2-pyridinyl]phenyl]methyl]imidazo[4,5-b]pyridine

EXAMPLE 19

2-propyl-4-methyl-1-[4-[3-(1H-tetrazol-5-yl)-4-pyridinyl]phenyl]methylbenzimidazole Step A: Preparation of 2-propyl-4-methyl-1-[4-(3-cyano)-4-pyridinyl]phenyl]methylbenzimidazole The title compound may be prepared by treatment of 2-propyl-4-methylbenzimidazole (prepared as in European Patent Application 400,835, 1990) with one equivalent of NaH in anhydrous DMF at 20° C. for 10 minutes followed by addition of one equivalent of 3-cyano-4-(4-bromomethylphenyl)pyridine and stirring for 24 hours. The crude product may be purified by concentrating the reaction mixture under reduced pressure and subsequent flash chromatography (SiO₂, EtOAc-hexanes elution).

Step B: Preparation of 2-propyl-4-methyl-1-[4-[3-(1H-tetrazol-5-yl)-4-pyridinyl]phenyl]methylbenzimidazole The title compound may be prepared by treatment of 2-propyl-4-methyl-1-[4-[3-cyano-4-pyridinyl]phenyl]-methylbenzimidazole with one or more equivalents of Me₃SnN₃ in toluene at reflux over a period of 1-3 days. The title compound may be purified in a manner similar to that stated in Example 1, Step F.

EXAMPLE 20

6-Methyl-2-(morpholin-4-yl)-8-propyl-9-[4-[3-(1H-tetrazol-5-yl)-4-pyridinyl]phenyl]methylpurine Step A: Preparation of 6-methyl-2-(morpholin-4-yl)-8-propyl-9-[4-(3-cyano)-4-pyridinyl]phenyl]methylpurine The title compound may be prepared by treatment of 6-methyl-2-(morpholine-4-yl)-8-propylpurine (prepared as in European Patent Application 400,974, 1990) with one equivalent of NaH in anhydrous DMF at 20° C. for 10 minutes, followed by addition of one equivalent of 3-cyano-4-(4-bromomethylphenyl)pyridine and stirring for 24 hours. The title compound may be purified in a manner similar to that stated in Example 19, Step A.

Step B: Preparation of 6-methyl-2-(morpholin-4-yl)-8-propyl-9-[4-[3-(1H-tetrazol-5-yl)-4-pyridinyl]phenyl]-methylpurine The title compound may be prepared by treatment of 6-methyl-2-(morpholine-4-yl)-8-propyl-9-[4-(3-cyano)-4-pyridinyl]phenyl]methylpurine by treatment with one or more equivalents of Me₃SnN₃ in toluene at reflux over a period of 1-3 days. The title compound may be purified in a manner similar to that stated in Example 1, Step F.

EXAMPLE 21

6-methyl-2-methylamino-8-propyl-9-[4-[3-(1H-tetrazol-5-yl)-4-pyridinyl]phenyl]methylpurine Step A: Preparation of 6-methyl-2-methylamino-8-propyl-9-[4-(3-cyano)-4-pyridinyl]phenyl]methylpurine The title compound may be prepared by treatment of 6-methyl-2-methylamino-8-propylpurine (prepared as in European Patent Application 400,974, 1990) with one equivalent of NaH in anhydrous DMF at 20° C. for 10 minutes, followed by addition of one equivalent of 3-cyano-4-(4-bromomethylphenyl)pyridine and stirring for 24 hours. The title compound may be purified in a manner similar to that stated in Example 19, Step A.

Step B: Preparation of 6-methyl-2-methylamino-8-propyl-9-[4-[3-(1H-tetrazol-5-yl)-4-pyridinyl]phenyl]methylpurine The title compound may be prepared by treatment of 6-methyl-2-methylamino-8-propyl-9-[4-(3-cyano)-4-pyridinyl]phenyl]methylpurine by treatment with one or more equivalents of $Me_3SnN_3$ in toluene at reflux over a period of 1-3 days. The title compound may be purified in a manner similar to that stated in Example 1, Step F.

What is claimed is:

1. A compound or a pharmaceutically acceptable salt of structural formula

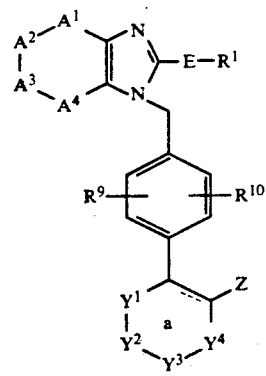

wherein:

$R^1$ is:

(a) $(C_1-C_6)$-alkyl, $(C_2-C_6)$-alkenyl or $(C_2-C_6)$-alkynyl each of which can be unsubstituted or substituted with a substituent selected from the group consisting of:
  i) aryl as defined below in $R^1$(b),
  ii) $(C_3-C_7)$-cycloalkyl,
  iii) Cl, Br, I, F,
  iv) OH,
  v) $NH_2$,
  vi) $NH(C_1-C_4)$-alkyl,
  vii) $N[(C_1-C_4)$-alkyl$]_2$,
  viii) $NHSO_2R^2$,
  ix) $CF_3$,
  x) $COOR^2$, or
  xi) $SO_2NHR^2$, (b) aryl, wherein aryl is defined as phenyl or naphthyl, unsubstituted or substituted with 1 or 2 substituents selected from the group consisting of:
  i) Cl, Br, I, F,
  ii) $(C_1-C_4)$-alkyl,
  iii) $(C_1-C_4)$-alkoxy,
  iv) $NO_2$,
  v) $CF_3$,
  vi) $SO_2NR^2R^2$,
  vii) $(C_1-C_4)$-alkylthio,
  viii) hydroxy,
  ix) amino,
  x) $(C_3-C_7)$-cycloalkyl,
  xi) $(C_3-C_{10})$-alkenyl, (c) heteroaryl, wherein heteroaryl is defined as a 5- or 6-membered heteroaromatic moiety, which can contain one or two members selected from the group consisting of N, O, S and wherein the heteroaryl is unsubstituted, monosubstituted or disubstituted with substituents selected from the group consisting of:
  i) Cl, Br, I, F,
  ii) OH,
  iii) SH,
  iv) $NO_2$,
  v) $(C_1-C_4)$-alkyl,
  vi) $(C_2-C_4)$-alkenyl,
  vii) $(C_2-C_4)$-alkynyl,
  viii) $(C_1-C_4)$-alkoxy, or
  ix) $CF_3$, (d) $(C_1-C_4)$-perfluoroalkyl, or (e) $(C_3-C_7)$-cycloalkyl, which can be substituted or unsubstituted with a substituent selected from the group consisting of: $(C_1-C_4)$-alkyl, $(C_1-C_4)$-perfluoroalkyl, Cl, Br, I, or F;

—$A^1$—$A^2$—$A^3$—$A^4$— represents:

(a) 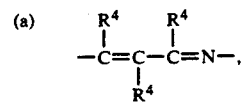

(b) 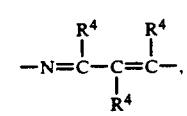

(c) 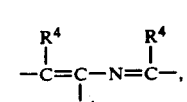

(d) 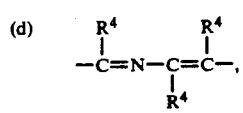

(e) 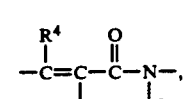

(f) 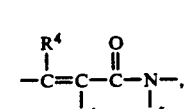

(g) 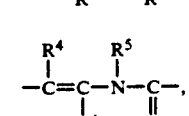

(h) 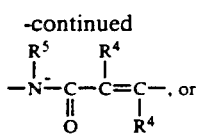, or (i) 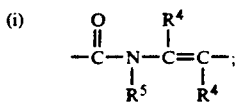;

E is:
(a) a single bond,
(b) —S(O)$_n$(CH$_2$)$_s$—, or
(c) —O—;

n is 0 to 2;
s is 0 to 5;

R$^2$ is:
(a) H,
(b) (C$_1$–C$_6$)-alkyl,
(c) —CH$_2$—O—C(O)CH$_3$,
(d) CH$_2$-aryl, or
(e) aryl;

R$^4$ group are independently:
(a) H,
(b) (C$_1$–C$_6$)-alkyl, (C$_2$–C$_6$)-alkenyl, (C$_2$–C$_6$)-alkynyl or (C$_3$–C$_8$)-cycloalkyl, each of which is unsubstituted or substituted with:
  i) OH,
  ii) (C$_1$–C$_4$)-alkoxy,
  iii) CO$_2$R$^2$,
  iv) OCOR$^2$,
  v) CONHR$^2$,
  vi) CON(R$^2$)$_2$,
  vii) N(R$^2$) C(O)R$^2$,
  viii) NH$_2$,
  ix) (C$_1$–C$_4$)-alkylamino,
  x) di[(C$_1$–C$_4$)-alkyl]amino,
  xi) aryl,
  xii) heteroaryl,
(c) —C(O)-aryl,
(d) —NO$_2$,
(e) Cl, Br, I, F,
(f) —OH,
(g) —OR$^{16}$,
(h) (C$_1$–C$_4$)-perifluoroalkyl,
(i) —SH,
(j) —S(O)$_n$—(C$_1$–C$_4$)-alkyl,
(k) —CO$_2$R$^2$,
(l) —SO$_3$H,
(m) —NR$^2$R$^{16}$,
(n) —NR$^2$C(O)R$^{16}$,
(o) —NR$^2$COOR$^{14}$,
(p) —SO$_2$NHR$^{14}$,
(q) —SO$_2$NR$^2$R$^2$,
(r) —NHSO$_2$R$^{14}$,
(s) —C(O)NHSO$_2$R$^{14}$,
(t) aryl,
(u) heteroaryl,
(v) morpholin-4-yl,
(w) CONH$_2$, or
(y) 1H-tetrazol-5-yl;

R$^5$ is:
(a) H,
(b) (C$_1$–C$_6$)-alkyl, (C$_2$–C$_6$)-alkenyl or (C$_2$–C$_6$)-alkynyl each of which can be unsubstituted or substituted with a substituent selected from the group consisting of: (C$_3$–C$_7$)-cycloalkyl, Cl, Br, I, F, —OH, —NH$_2$, —NH[(C$_1$–C$_4$)-alkyl], —N[(C$_1$–C$_4$)-alkyl]$_2$, —NHSO$_2$R$^{18}$, —CO$_2$R$^{18}$, (C$_1$–C$_4$)-alkoxy, (C$_1$–C$_4$)-alkylthio, (C$_1$–C$_4$)-acyl, or C(=O)NH$_2$,
(c) aryl, unsubstituted or substituted with V or W as defined below, or
(d) aryl-(C$_1$–C$_4$)-alkyl, unsubstituted or substituted with V or W as defined below;

—Y$^1$—Y$^2$—Y$^3$—Y$^4$— is:
(a) —N=CR$^{11}$—CR$^{11}$=CR$^{11}$—,
(b) —CR$^{11}$=N—CR$^{11}$=CR$^{11}$—,
(c) —CR$^{11}$=CR$^{11}$—N=CR$^{11}$—,
(d) —CR$^{11}$=CR$^{11}$—CR$^{11}$=N—, (e) 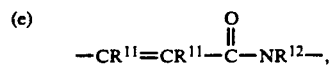

(f) 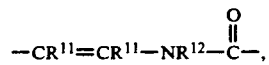

(g) 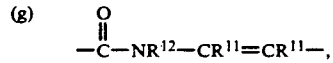

(h) 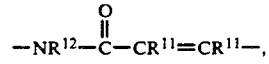

wherein a represents a double bond in each of the above definitions (a) thru (h)

(i) 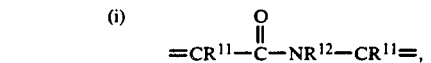

(j) 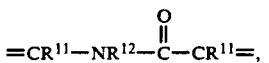

wherein a represents a single bond in each of the above definitions (i) thru (j);

R$^9$ and R$^{10}$ are each independently:
(a) H,
(b) Cl, Br, I, F,
(c) NO$_2$,
(d) (C$_1$–C$_6$)-alkyl,
(e) (C$_1$–C$_6$)-acyloxy,
(f) (C$_3$–C$_6$)-cycloalkyl,
(g) (C$_1$–C$_6$)-alkoxy,
(h) —NHSO$_2$R$^2$,
(i) hydroxy-(C$_1$–C$_4$)-alkyl,
(j) aryl-(C$_1$–C$_4$)-alkyl,
(k) (C$_1$–C$_4$)-alkylthio,
(l) (C$_1$–C$_4$)-alkylsulfinyl,
(m) (C$_1$–C$_4$)-alkylsulfonyl,
(n) NH$_2$,
(o) (C$_1$–C$_4$)-alkylamino,
(p) (C$_1$–C$_4$)-dialkylamino,
(q) CF$_3$,
(r) —SO$_2$NHR$^2$,
(s) furyl,
(t) aryl, wherein aryl is phenyl or naphthyl, unsubstituted or substituted with one or two substituents selected from the group consisting of: Cl, Br, I, F, (C$_1$–C$_4$)-alkyl, (C$_1$–C$_4$)-alkoxy, NO$_2$, CF$_3$, (C$_1$–C$_4$)-alkylthio, OH, NH$_2$, —NH[C$_1$–C$_4$)-alkyl], —N[(C$_1$–C$_4$)-alkyl]$_2$, —CO$_2$H, or —CO$_2$—(C$_1$–C$_4$)-alkyl, or
(u) when R$^9$ and R$^{10}$ are bonded to adjacent carbon atoms, they can be joined to form an aryl ring;

$R^{11}$ is:
 (a) H,
 (b) Cl, Br, I, F,
 (c) $NO_2$,
 (d) $NH_2$,
 (e) $(C_1-C_4)$-alkylamino,
 (f) di-$(C_1-C_4$-alkyl)amino
 (g) $SO_2NHR^2$,
 (h) $CF_3$,
 (i) $(C_1-C_4)$-alkyl,
 (j) $(C_1-C_4)$-alkoxy, or
 (k) when two $R^{11}$ substituents are bonded to adjacent carbon atoms, they can be joined to form an aryl ring;

$R^{12}$ is:
 (a) H,
 (b) $(C_1-C_4)$-alkyl, or
 (c) phenyl or —$CH_2$-phenyl, in which the phenyl is unsubstituted or substituted with one or two substituents selected from the group consisting of: Cl, Br, I, F, $(C_1-C_4)$-alkyl, or $(C_1-C_4)$-alkoxy, $CF_3$, $NH[(C_1-C_4)$-alkyl], $N[(C_1-C_4)$-alkyl]$_2$, $NH_2$ or $CO_2R^2$;

Z is:
 (a) —$CO_2R^2$,
 (b) —$SO_3R^{13}$,
 (c) —$NHSO_2R^{14}$,
 (d) —$PO(OR^{13})_2$,
 (e) —$SO_2NHR^{14}$,
 (f) —$CONHOR^{13}$, (g) 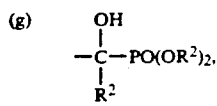

(h) —CN,
 (i) —$SO_2NH$-heteroaryl, wherein heteroaryl is an unsubstituted, monosubstituted or disubstituted five or six membered aromatic ring which can contain from 1 to 3 heteroatoms selected from the group consisting of O, N or S and wherein the substituents are members selected from the group consisting of: —OH, —SH, —$(C_1-C_4)$-alkyl, —$(C_1-C_4)$-alkoxy, —$CF_3$, Cl, Br, F, I, —$NO_2$, —$CO_2H$, —$CO_2$—$(C_1-C_4)$-alkyl, —$NH_2$, $NH[(C_1-C_4)$-alkyl] or —$N[(C_1-C_4)$-alkyl]$_2$,
 (j) —$CH_2SO_2NH$-heteroaryl,
 (k) —$SO_2NHC(O)R^{14}$,
 (l) —$CH_2SO_2NHC(O)R^{14}$,
 (m) —$C(O)NHSO_2R^{14}$,
 (n) —$CH_2C(O)NHSO_2R^{14}$,
 (o) —$NHSO_2NHC(O)R^{14}$,
 (p) —$NHC(O)NHSO_2R^{14}$, (q) 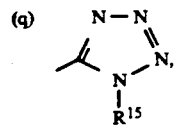

(r) 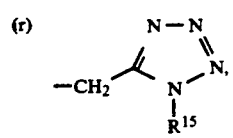

(s) 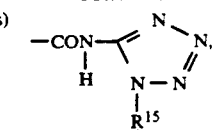

(t) —$CONHNHSO_2CF_3$, (u) 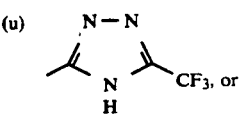

(v) 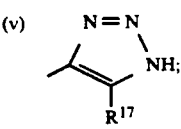

$R^{13}$ is H, —$CH_2$-phenyl or —$CH(R^4)$—O—$C(O)R^4$;

$R^{14}$ is
 (a) aryl,
 (b) heteroaryl,
 (c) $(C_3-C_7)$-cycloalkyl,
 (d) $(C_1-C_4)$-alkyl, unsubstituted or substituted with a substituent selected from the group consisting of: aryl, heteroaryl, —OH, —SH, $(C_1-C_4)$-alkyl, $(C_1-C_4)$-alkoxy, $(C_1-C_4)$-alkylthio, —$CF_3$, Cl, Br, F, I, —$NO_2$, —$CO_2H$, $CO_2$—$(C_1-C_4)$-alkyl, —$NH_2$, —$N[(C_1-C_4)$-alkyl]$_2$, —$NH[(C_1-C_4)$-alkyl], —$PO_3H$ or $PO(OH)(C_1-C_4)$-alkyoxy, or
 (e) $(C_1-C_4)$-perfluoroalkyl;

$R^{15}$ is
 (a) H,
 (b) $(C_1-C_6)$-alkyl,
 (c) $(C_2-C_4)$-alkenyl,
 (d) $(C_1-C_4)$-alkoxyalkyl,
 (e) —$CH_2O$—$C(O)CH_3$, or
 (f) —$CH_2$-phenyl, wherein the phenyl is unsubstituted or substituted with a substituent selected from the group consisting of: —$NO_2$, —$NH_2$, —OH or —$OCH_3$;

$R^{16}$ is:
 (a) H, or
 (b) $(C_1-C_4)$-alkyl unsubstituted or substituted with:
  i) $NH_2$,
  ii) $NH[(C_1-C_4)$-alkyl],
  iii) $N[(C_1-C_4)$-alkyl]$_2$,
  iv) $CO_2H$,
  v) $CO_2(C_1-C_4)$-alkyl,
  vi) OH,
  vii) $SO_3H$, or
  viii) $SO_2NH_2$;

$R^{17}$ is —CN, —$NO_2$, —$CO_2R^2$, $(C_1-C_6)$-perfluoroalkyl or —$CF_3$;

$R^{18}$ is:
 (a) H,
 (b) $(C_1-C_6)$-alkyl,
 (c) aryl, or
 (d) $(C_1-C_5)$-alkyl-aryl; and V and W are each independently selected from:
 (a) H,
 (b) $(C_1-C_5)$-alkoxy,
 (c) $(C_1-C_5)$-alkyl,
 (d) hydroxy,
 (e) $(C_1-C_5)$-alkyl-$S(O)_n$, (f) —CN,
(g) —NO$_2$,
(h) —NR$^2$R$^2$,
(i) (C$_1$-C$_5$)-acyl-NR$^2$R$^2$,
(j) —CO$_2$R$^2$,
(k) (C$_1$-C$_5$)-alkyl-carbonyl,
(l) CF$_3$,
(m) I, Br, Cl, F,
(n) hydroxy-(C$_1$-C$_4$)-alkyl-,
(o) carboxy-(C$_1$-C$_4$)-alkyl-,
(p) —1H-tetrazol-5-yl,
(q) —NH—SO$_2$CF$_3$, or
(r) aryl.

2. The compound of claim 1 wherein:
R$^1$ is:
  (a) (C$_1$-C$_6$)-alkyl, (C$_2$-C$_6$)-alkenyl or (C$_2$-C$_6$)-alkynyl each of which can be unsubstituted or substituted with a substituent selected from the group consisting of:
    i) aryl, wherein aryl is defined as phenyl or naphthyl, unsubstituted or substituted with 1 or 2 substituents selected from the group consisting of: Cl, Br, I, F, (C$_1$-C$_4$)-alkyl, (C$_1$-C$_4$)-alkoxy, NO$_2$, CF$_3$, SO$_2$NR$^2$R$^2$, (C$_1$-C$_4$)-alkylthio, hydroxy, amino, (C$_3$-C$_7$)-cycloalkyl, or (C$_3$-C$_{10}$)-alkenyl,
    ii) (C$_3$-C$_7$)-cycloalkyl,
    iii) Cl, Br, I, F,
    iv) OH,
    v) NH$_2$,
    vi) NH(C$_1$-C$_4$)-alkyl,
    vii) N[(C$_1$-C$_4$)-alkyl)]$_2$,
    viii) NHSO$_2$R$^2$,
    ix) CF$_3$,
    x) COOR$^2$, or
    xi) SO$_2$NHR$^2$,
  (b) (C$_1$-C$_4$)-perfluoroalkyl, or
  (c) (C$_3$-C$_7$)-cycloalkyl, which can be substituted or unsubstituted with a substituent selected from the group consisting of: (C$_1$-C$_4$)-alkyl, (C$_1$-C$_4$)-perfluoroalkyl, Cl, Br, I or F;
—A$^1$—A$^2$—A$^3$—A$^4$— represent:

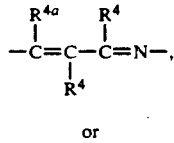

(a)

or

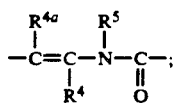

(b)

E is: a single bond;
R$^2$ is:
  (a) H,
  (b) (C$_1$-C$_6$)-alkyl,
  (c) —CH$_2$—O—C(O)CH$_3$,
  (d) CH$_2$-aryl, or
  (e) aryl;
R$^{4a}$ is:
  (a) H,
  (b) (C$_1$-C$_6$)-alkyl,
  (c) (C$_2$-C$_6$)-alkenyl,
  (d) (C$_2$-C$_4$)-alkynyl,
  (e) (C$_3$-C$_6$)-cycloalkyl,
  (f) (C$_1$-C$_6$)-perfluoroalkyl, or
  (g)(C$_1$-C$_6$)-alkyl-(C$_3$-C$_6$)-cycloalkyl;
R$^4$ groups are independently:
  (a) H,
  (b) (C$_1$-C$_6$)-alkyl, (C$_2$-C$_6$)-alkenyl, (C$_2$-C$_6$)-alkynyl or (C$_3$-C$_8$)-cycloalkyl, each of which is unsubstituted or substituted with:
    i) OH,
    ii) (C$_1$-C$_4$)-alkoxy,
    iii) CO$_2$R$^2$,
    iv) OCOR$^2$,
    v) CONHR$^2$,
    vi) CON(R$^2$)$_2$,
    vii) N(R$^2$)C(O)R$^2$,
    viii) NH$_2$,
    ix) (C$_1$-C$_4$)-alkylamino,
    x) di[(C$_1$-C$_4$)-alkyl]amino,
    xi) aryl,
    xii) heteroaryl,
  (c) —C(O)—aryl,
  (d) —NO$_2$,
  (e) Cl, Br, I, F,
  (f) —OH,
  (g) —OR$^{16}$,
  (h) —CF$_3$,
  (i) —SH,
  (j) —S(O)$_n$—(C$_1$-C$_4$)-alkyl,
  (k) —CO$_2$R$^2$,
  (l) —SO$_3$H,
  (m) —NR$^2$R$^{16}$,
  (n) —NR$^2$C(O)R$^{16}$,
  (o) —NR$^2$COOR$^{14}$,
  (p) —SO$_2$NHR$^{14}$,
  (q) —SO$_2$NR$^2$R$^2$,
  (r) —NHSO$_2$R$^{14}$,
  (s) —C(O)NHSO$_2$R$^{14}$,
  (t) aryl,
  (u) heteroaryl, or
  (v) morpholin-4-yl; and
R$^5$ is:
  (a) H,
  (b) (C$_1$-C$_6$)-alkyl, (C$_2$-C$_6$)-alkenyl or (C$_2$-C$_6$)-alkynyl each of which can be unsubstituted or substituted with a substituent selected from the group consisting of: (C$_3$-C$_7$)-cycloalkyl, Cl, Br, I, F, —OH, —NH$_2$, —NH[(C$_1$-C$_4$)-alkyl], —N[(C$_1$-C$_4$)-alkyl]$_2$, —NHSO$_2$R$^{18}$, —CO$_2$R$^{18}$, (C$_1$-C$_4$)-alkoxy, (C$_1$-C$_4$)-alkylthio, (C$_1$-C$_4$)-acyl, or C(=O)NH$_2$,
  (c) aryl, unsubstituted or substituted with V or W as defined below, or
  (d) aryl-(C$_1$-C$_4$)-alkyl, unsubstituted or substituted with V or W as defined below;
—Y$^1$—Y$^2$—Y$^3$—Y$^4$— is:
  (a) —N=CR$^{11}$—CR$^{11}$=CR$^{11}$—,
  (b) —CR$^{11}$=N—CR$^{11}$=CR$^{11}$—,
  (c) —CR$^{11}$=CR$^{11}$—N=CR$^{11}$—, or
  (d) —CR$^{11}$=CR$^{11}$—CR$^{11}$=N—,
  wherein a represents a double bond in each of the above definitions;
R$^9$ and R$^{10}$ are each independently:
  (a) H,
  (b) Cl, Br, I, F,
  (c) CF$_3$,
  (d) (C$_1$-C$_6$)-alkyl,
  (e) (C$_1$-C$_6$)-acyloxy,
  (f) (C$_3$-C$_6$)-cycloalkyl,
  (g) (C$_1$-C$_6$)-alkoxy, (h) hydroxy-($C_1$-$C_4$)-alkyl,
(i) aryl-($C_1$-$C_4$)-alkyl,
(j) ($C_1$-$C_4$)-alkylthio,
(k) ($C_1$-$C_4$)-alkylsulfinyl,
(l) ($C_1$-$C_4$)-alkylsulfonyl, or
(m) when $R^9$ and $R^{10}$ are bonded to adjacent carbon atoms, they can be joined to form an aryl ring;

$R^{11}$ is:
(a) H,
(b) Cl, Br, I, F,
(c) $NO_2$,
(d) $NH_2$,
(e) ($C_1$-$C_4$)-alkylamino,
(f) di-($C_1$-$C_4$-alkyl)amino
(g) $SO_2NHR^2$,
(h) $CF_3$,
(i) ($C_1$-$C_4$)-alkyl,
(j) ($C_1$-$C_4$)-alkoxy, or
(k) when two $R^{11}$ substituents are bonded to adjacent carbon atoms, they can be joined to form an aryl ring;

$R^{12}$ is:
(a) H,
(b) ($C_1$-$C_4$)-alkyl, or
(c) phenyl or —$CH_2$-phenyl, in which the phenyl is unsubstituted or substituted with one or two substituents selected from the group consisting of: Cl, Br, I, F, ($C_1$-$C_4$)-alkyl, or ($C_1$-$C_4$)-alkoxy, $CF_3$, NH[($C_1$-$C_4$)-alkyl], N[($C_1$-$C_4$)-alkyl]$_2$, $NH_2$ or $CO_2R^2$;

Z is:
(a) —$CO_2R^2$,
(b) —CN,
(c) —$SO_2$NH-heteroaryl, wherein heteroaryl is an unsubstituted, monosubstituted or disubstituted five or six membered aromatic ring which can contain from 1 to 3 heteroatoms selected from the group consisting of O, N or S and wherein the substituents are members selected from the group consisting of: —OH, —SH, —($C_1$-$C_4$)-alkyl, —($C_1$-$C_4$)-alkoxy, —$CF_3$, Cl, Br, F, I, —$NO_2$, —$CO_2$H, —$CO_2$—($C_1$-$C_4$)-alkyl, —$NH_2$, NH[($C_1$-$C_4$)-alkyl] or —N[($C_1$-$C_4$)-alkyl]$_2$,
(d) —$CH_2SO_2$NH-heteroaryl,
(e) —$SO_2$NHC(O)$R^{14}$,
(f) —C(O)NHSO$_2R^{14}$,
(g) —NHSO$_2R^{14}$, or
(h) —1H-tetrzol-5-yl;

$R^{14}$ is
(a) aryl,
(b) heteroaryl,
(c) ($C_3$-$C_7$)-cycloalkyl,
(d) ($C_1$-$C_4$)-alkyl, unsubstituted or substituted with a substituent selected from the group consisting of: aryl, heteroaryl, —OH, —SH, ($C_1$-$C_4$)-alkyl, ($C_1$-$C_4$)-alkoxy, ($C_1$-$C_4$)-alkylthio, —$CF_3$, Cl, Br, F, I, —$NO_2$, —$CO_2$H, $CO_2$—($C_1$-$C_4$)-alkyl, —$NH_2$, —N[($C_1$-$C_4$)-alkyl]$_2$, —NH[($C_1$-$C_4$)-alkyl], —$PO_3$H, PO(OH)($C_1$-$C_4$)-alkyoxy, or
(e) ($C_1$-$C_4$)-perfluoroalkyl;

$R^{16}$ is:
(a) H, or
(b) ($C_1$-$C_4$)-alkyl unsubstituted or substituted with:
i) $NH_2$,
ii) NH[($C_1$-$C_4$)-alkyl],
iii) N[($C_1$-$C_4$)-alkyl]$_2$,
iv) $CO_2$H,
v) $CO_2$($C_1$-$C_4$)-alkyl,
vi) OH,
vii) $SO_3$H, or
viii) $SO_2NH_2$;

$R^{18}$ is:
(a) H,
(b) ($C_1$-$C_6$)-alkyl,
(c) aryl, or
(d) aryl-($C_1$-$C_5$)-alkyl;

V and W are each independently selected from:
(a) H,
(b) ($C_1$-$C_5$)-alkoxy,
(c) ($C_1$-$C_5$)-alkyl,
(d) hydroxy,
(e) ($C_1$-$C_5$)-alkyl-S(O)$_n$,
(f) —CN,
(g) —$NO_2$,
(h) —$NR^2R^2$,
(i) ($C_1$-$C_5$)-acyl-$NR^2R^2$,
(j) —$CO_2R^2$,
(k) ($C_1$-$C_5$)-alkyl-carbonyl,
(l) $CF_3$,
(m) I, Br, Cl, F,
(n) hydroxy-($C_1$-$C_4$)-alkyl-,
(o) carboxy-($C_1$-$C_4$)-alkyl-,
(p) —tetrazol-5-yl,
(q) —NHSO$_2$CF$_3$, or
(r) aryl.

3. The compound of claim 1 of structural formula or its pharmaceutically acceptable salt

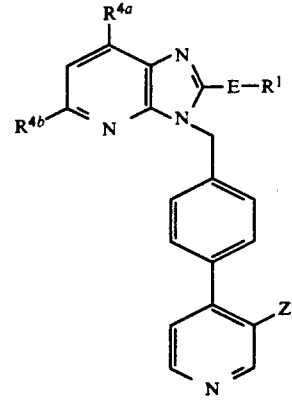

wherein:
$R^1$ is
a) ($C_1$-$C_6$)-alkyl,
b) ($C_3$-$C_7$)-cycloalkyl, or
c) ($C_1$-$C_4$)-alkyl-($C_3$-$C_7$)-cycloalkyl;
E is: single bond, O, or S;
$R^{4a}$ is:
(a) H,
(b) ($C_1$-$C_4$)-alkyl,
(c) ($C_1$-$C_4$)-perfluoroalkyl,
(d) ($C_1$-$C_3$)-alkoxyl,
(e) ($C_1$-$C_3$)-alkylthio,
(f) ($C_3$-$C_8$)-cycloalkyl, or
(g) F, Cl;
$R^{4b}$ is:
(a) $R^{4a}$,
(b) ($C_1$-$C_6$)-alkyl, ($C_2$-$C_6$)-alkenyl, substituted with a substituent selected from the group consisting of:
i) $CO_2R^2$,
ii) aryl, or
iii) heteroaryl, (c) —OH,
(d) —CF₃,
(e) —CO₂R²,
(f) —NR²R¹⁶,
(g) —CO₂NH₂,
(h) —CONHSO₂R¹⁴,
(i) 1H-tetrazol-5-yl,
(j) aryl,
(k) heteroaryl, or
(l) morpholin-4-yl;

Z is:
(a) CO₂R²,
(b) 1H-tetrazol-5-yl,
(c) CONHSO₂R¹⁴,
(d) SO₂NHR¹⁴,
(e) NHSO₂R¹⁴,
(f) SO₂NHCOR¹⁴, or
(g) NHSO₂CF₃.

4. The compound of claim 1 of structural formula or its pharmaceutically acceptable salt

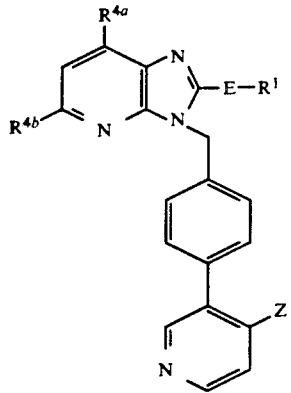

wherein:
R¹ is
  a) (C₁–C₆)-alkyl,
  b) (C₃–C₇)-cycloalkyl, or
  c) —(C₁–C₄)-alkyl-(C₃–C₇)-cycloalkyl;
E is: single bond, O, or S;
R⁴ᵃ is:
  (a) H,
  (b) (C₁–C₄)-alkyl,
  (c) (C₁–C₄)-perfluoroalkyl,
  (d) (C₁–C₃)-alkoxyl,
  (e) (C₁–C₃)-alkylthio,
  (f) (C₃–C₈)-cycloalkyl, or
  (g) F, Cl;
R⁴ᵇ is:
  (a) R⁴ᵃ,
  (b) (C₁–C₆)-alkyl, (C₂–C₆)-alkenyl, substituted with a substituent selected from the group consisting of:
    i) CO₂R²,
    ii) aryl, or
    iii) heteroaryl,
  (c) —OH,
  (d) —CF₃,
  (e) —CO₂R²,
  (f) —NR²R¹⁶,
  (g) —CO₂NH₂,
  (h) —CONHSO₂R¹⁴,
  (i) 1H-tetrazol-5-yl,
  (j) aryl,
  (k) heteroaryl, or
  (l) morpholin-4-yl;

Z is:
  (a) CO₂R²,
  (b) 1H-tetrazol-5-yl,
  (c) CONHSO₂R¹⁴,
  (d) SO₂NHR¹⁴,
  (e) NHSO₂R¹⁴,
  (f) SO₂NHCOR¹⁴, or
  (g) NHSO₂CF₃.

5. The compound of claim 1 selected from the group consisting of:
7-Methyl-2-propyl-3-[[4-[3-(1H-tetrazol-5-yl)-4-pyridinyl]phenyl]methyl]imidazo[4,5-b]pyridine;
5,7-Dimethyl-2-ethyl-3-[[4-[3-(1H-tetrazol-5-yl)-4-pyridinyl]phenyl]methyl]imidazo[4,5-b]pyridine;
Methyl 2-ethyl-7-methyl-3-[[4-[3-(1H-tetrazol-5-yl)-4-pyridinyl]phenyl]methyl]imidazo[4,5-b]pyridine-5-carboxylate;
Methyl 7-methyl-2-propyl-3-[[4-[3-(1H-tetrazol-5-yl)-4-pyridinyl]phenyl]methyl]imidazo[4,5-b]pyridine-5-carboxylate;
7-Methyl-2-propyl-3-[[4-[3-(1H-tetrazol-5-yl)-2-pyridinyl]phenyl]methyl]imidazo[4,5-b]pyridine-5-carboxylic acid;
2-Ethyl-7-methyl-3-[[4-[3-(1H-tetrazol-5-yl)-2-pyridinyl]phenyl]methyl]imidazo[4,5-b]pyridine-5-carboxylic acid;
7-Methyl-2-propyl-3-[[4-[2-(1H-tetrazol-5-yl)-3-pyridinyl]phenyl]methyl]imidazo[4,5-b]pyridine;
5,7-Dimethyl-2-ethyl-3-[[4-[2-(1H-tetrazol-5-yl)-3-pyridinyl]phenyl]methyl]imidazo[4,5-b]pyridine;
Methyl 2-ethyl-7-methyl-3-[[4-[2-(1H-tetrazol-5-yl)-3-pyridinyl]phenyl]methyl]imidazo[4,5-b]pyridine-5-caboxlate;
Methyl 7-methyl-2-propyl-3-[[4-[2-(1H-tetrazol-5-yl)-3-pyridinyl]phenyl]methyl]imidazo[4,5-b]pyridine-5-carboxylate;
7-Methyl-2propyl-3-[[4-[2(1H-tetrazol-5-yl)-3-pyridinyl]phenyl]methyl]imidazo[4,5-b]pyridine-5-carboxylic acid;
2-Ethyl-7-methyl-3-[[4-[2-(1H-tetrazol-5-yl)3-pyridinyl]phenyl]methyl]imidazo[4,5-b]pyridine-5-carboxylic acid;
7-Methyl-2-propyl-3-[[4-[3-(1H-tetrazol-5-yl)-2-pyridinyl]phenyl]methyl]imidazo[4,5-b]pyridine;
7-Methyl-2-propyl-3-[[4-(3-(1H-tetrazol-5-yl)-2-pyridinyl]phenyl]methyl]imidazo[4,5-b]pyridine-5-carboxylic acid;
2-Ethyl-7-methyl-3-[[4-[3-(1H-tetrazol-5-yl)-2-pyridinyl]phenyl]methyl]imidazo[4,5-b]pyridine-5-carboxylic acid;
5,7-Dimethyl-2-ethyl-3-[[4-[3-(1H-tetrazol-5-yl)-2-pyridinyl]phenyl]methyl]imidazo[4,5-b]pyridine;
Methyl 2-ethyl-7-methyl-3-[[4-[3-(1H-tetrazol-5-yl)-2-pyridinyl]phenyl]methyl]imidazo[4,5-b]pyridine-5-carboxylate; or
Methyl 7-methyl-2-propyl-3-[[4-[3-(1H-tetrazol-5-yl)-2-pyridinyl]phenyl]methyl]imidazo[4,5-b]pyridine-5-carboxylate.

6. The compound of claim 1 selected from the group consisting of:
7-methyl-2-propyl-3-[[4-[3-(1H-tetrazol-5-yl)-4-pyridinyl]phenyl]methyl]imidazo[4,5-b]pyridine;
7-methyl-2-ethyl-3-[[4-[3-(1H-tetrazol-5yl)-4-pyridinyl]phenyl]methyl]imidazo[4,5-b]pyridine;
5,7-dimethyl-2-ethyl-3[[4-[3-(1H-tetrazol-5-yl)-4-pyridinyl]phenyl]methyl]imidazo[4,5-b]pyridine;

2-ethyl-7-methyl-3[[4-[3-(1H-tetrazol-5-yl)-4-pyridinyl]-phenyl]methyl]imidazo[4,5-b]pyridine-5-carboxylic acid;
ethyl 2-ethyl-7-methyl-3-[[4-[3-(1H-tetrazol-5-yl)-4-pyridinyl]phenyl]methyl]imidazo[4,5-b]pyridine-5-carboxylate;
5,7-dimethyl-2-ethyl-3-[[4-[3-(N-benzoylsulfonamido)-4-pyridinyl]phenyl]methyl]imidazo[4,5-b]pyridine;
5,7-dimethyl-2-ethyl-3[[4-[3-(N-cyclopropanecarbonylsulfonamido)-4-pyridinyl]phenyl]methyl]imidazo[4,5-b]-pyridine;
2-ethyl-7-methyl-3-[[4-[3-(N-benzoylsulfonamido)-4-pyridinyl]phenyl]methyl]imidazo[4,5-b]pyridine-5-carboxylic acid;
ethyl 2-ethyl-7-methyl-3[[4-[3-(N-benzoylsulfonamido(-4-pyridinyl]phenyl]methyl]imidazo[4,5-b]pyridine-5-carboxylate;
2-ethyl-7-methyl-3-[[4-[3-(N-cyclopropanecarbonylsulfonamido)-4-pyridinyl]phenyl]methyl]imidazo[4,5-]-pyridine-5-carboxylic acid;
ethyl 2-ethyl-7-methyl-3[[4-[3-(N-cyclopropanecarbonylsulfonamido)-4-pyridinyl]phenyl]methyl]imidazo[4,5-b]pyridine-5-carboxylate;
5,7-dimethyl-2-ethyl-3-[[4-[3-(trifluoromethanesulphonamido)-4-pyridinyl]phenyl]methyl]imidazo[4,5-b]pyridine;
5,7-dimethyl-2-ethyl-3[[4-[3-(N-phenylsulfonylcarboxamido)-4-pyridinyl]phenyl]methyl]imidazo[4,5-b]pyridine;
5,7-dimethyl-2-ethyl-3-[[4-[4-(1H-tetrazol-5-yl)-3-pyridinyl]phenyl]methyl]imidazo[4,5-b]pyridine; or
5,7-dimethyl-2-ethyl-3-[[4-[4-(N-phenylsulfonylcarboxamido)-3-pyridinyl]phenyl]methyl]imidazo[4,5-b]pyridine.

7. A compound or its pharmaceutically acceptable salt selected from the group consisting of:
7-methyl-2-propyl-3-[[4-[3-(1H-tetrazol-5-yl)-4-pyridinyl]phenyl]methyl]imidazo[4,5-b]pyridine;
7-methyl-2-ethyl-3-[[4-[3-(1H-tetrazol-5-yl)-4-pyridinyl]phenyl]methyl]imidazo4,5-]pyridine;
5,7-dimethyl-2-ethyl-3-[[4-[3-(1H-tetrazol-5-yl)-4-pyridinyl]phenyl]methyl]imidazo[4,5-b]pyridine;
2-ethyl-7-methyl-3-[[4-[3-(1H-tetrazol-5-yl)-4-pyridinyl]phenyl]methyl] imidazo[4,5-b]pyridine-5-carboxylic acid;
ethyl 2-ethyl-7-methyl-3-[[4-[3-(1H-tetrazol-5-yl)-4-pyridinyl]methyl]imidazo[4,5-b]pyridine-5-carboxylate;
5,7-dimethyl-2-ethyl-3-[[4-[3-(N-benzoylsulfonamido)-4-pyridinyl]phenyl]methyl]imidazo[4,5-b]pyridine;
5,7-dimethyl-2-ethyl-3-[[4-[3-(N-cyclopropanecarbonylsulfonamido)-4-pyridinyl]phenyl]methyl]imidazo[4,5-b]pyridine;
2-ethyl-7-methyl-3-[[4-[3-(N-benzoylsulfonamido)-4-pyridinyl]phenyl]methyl]imidazo[4,5-b]pyridine-5-carboxylic acid;
ethyl 2-ethyl-7-methyl-3-[[4-[3-(N-benzoylsulfonamido)-4-pyridinyl]phenyl]methyl]imidazo[4,5-b]pyridine-5-carboxylate;
2-ethyl-7-methyl-3-[[4-[3-(N-cyclopropanecarbonylsulfonamido)-4-pyridinyl]phenyl]methyl]imidazo[4,5-b]pyridine-5-carboxylic acid;
ethyl 2-ethyl-7-methyl-3-[[4-[3-(N-cyclopropanecarbonylsulfonamido)-4-pyridinyl]phenyl]methyl]imidazo[4,5-b]pyridine-5-carboxylate;
5,7-dimethyl-2-ethyl-3-[[4-[3-(trifluoromethanesulfonamido)-4-pyridinyl]phenyl]methyl]imidazo4,5-b]pyridine; or
5,7-dimethyl-2-ethyl-3-[[4-[4-(1H-tetrazol-5-yl)-3-pyridinyl]phenyl]methyl]imidazo[4,5-b]pyridine.

8. A pharmaceutical composition useful in the treatment of hypertension which comprises a pharmaceutically acceptable carrier and a pharmaceutically effective amount of a compound of claim 1.

9. A method of treating hypertension which comprises administering to a patient in need of such treatment a pharmaceutically effective amount of a compound of claim 1.

10. An ophthalmological formulation for the treatment of ocular hypertension comprising an ophthalmologically acceptable carrier and an effective ocular antihypertensive amount of a compound of claim 1.

11. A method of treating ocular hypertension comprising administering to a patient in need of such treatment an effective ocular antihypertensive amount of a compound of claim 1.

12. A method of treating cognitive dysfunction, anxiety, or depression comprising administering to a patent in need of such treatment, a therapeutically effective amount of a compound of claim 1.

* * * * *

UNITED STATES PATENT AND TRADEMARK OFFICE
CERTIFICATE OF CORRECTION

PATENT NO. : 5,128,327
DATED : July 7, 1992
INVENTOR(S) : Prasun K. Chakravarty, et. al.

It is certified that error appears in the above-indentified patent and that said Letters Patent is hereby corrected as shown below:

On the Title page, item [75], "Malcolm MacCross" should read -- Malcolm MacCoss--.

Signed and Sealed this

Seventeenth Day of August, 1993

Attest:

BRUCE LEHMAN

Attesting Officer      Commissioner of Patents and Trademarks